(12) United States Patent
Poet et al.

(10) Patent No.: US 6,491,921 B1
(45) Date of Patent: Dec. 10, 2002

(54) AVIAN POLYOMAVIRUS VACCINES IN PSITTACINE BIRDS

(75) Inventors: Steven Poet, Winterville, GA (US); Branson W. Ritchie, Athens, GA (US); Victoria Burnley, Athens, GA (US); Denise Pesti, Athens, GA (US)

(73) Assignee: University of Georgia Research Foundation Inc., Athens, GA (US)

( * ) Notice: Subject to any disclaimer, the term of this patent is extended or adjusted under 35 U.S.C. 154(b) by 0 days.

(21) Appl. No.: 09/072,634

(22) Filed: May 4, 1998

Related U.S. Application Data

(63) Continuation-in-part of application No. 08/660,227, filed on Jun. 3, 1996, now Pat. No. 5,747,045, which is a continuation-in-part of application No. 08/180,929, filed on Jan. 13, 1994, now Pat. No. 5,523,088.

(51) Int. Cl.$^7$ .................... A61K 39/12; A61K 48/00; C07H 21/04; C07K 14/005; C12N 7/04

(52) U.S. Cl. ................ 424/186.1; 424/184.1; 424/204.1; 424/278; 424/1; 435/7.1; 435/69.3; 435/70.1; 435/235.1; 435/243; 435/320.1; 435/325; 514/44; 530/350; 536/23.72

(58) Field of Search .................... 424/186.1, 278.1, 424/204.1, 184.1; 435/7.1, 69.3, 70.1, 235.1, 243, 320.1, 325; 514/44; 530/350; 536/23.72

(56) References Cited

PUBLICATIONS

Ritchie et al., "Polyomavirus Infections in Adult Psittacine Birds" *J. Assoc. Avian Vet.* 5:202–206 (1991).
Graham and Calnek, "Papovavirus Infection in Hand–Fed Parrots: Virus Isolation and Pathology" *Avian Diseases* 31:398–410 (1985).
Ritchie et al., "Avian Polyomavirus: An Overview" *J. Assoc. Avian Vet.* 5:147–153 (1991).
Stoll et al., "Molecular and biological characteristics of avian polyomaviruses: isolates from different species of birds indicate that avian polymaviruses form a distinct subgenus within the polyomavirus genus" *J. Gen. Virology* 74:229–237 (1993).
Gaskin, J.M., "Adverse Reactions to Current Pet Bird Vaccines" *J. Assoc. Avian. Vet.* 5:12–14 (1991).
Sheets et al., "Studies of the effect of acemannan on retrovirus infections: clinical stabilization of feline lukemia virus infected cats" *Mol. Biother.* 3:41–45 (1991).
Lehn and Muller, "Cloning and characterization of budgerigar fledgling disease virus, an avian polyomavirus" *Virology* 151:362–370 (1986).
Niagro et al., "Polymerase chain reaction for detection of BFD in suspect birds" *Proc. Assoc. Avian Vet.*, Phoenix, 25–27 (1990).
Phalen et al., "Polymerase chain reaction assay for avain polyomavirus" *J. Clin. Microbiol.* 29:1030–1037 (1991).

Fogleman et al., "Toxicologic Evaluation of Injectible Acemannan in the Mouse, Rat and Dog" *Vet. Hum. Toxicol.* 3:201–205 Jun. (1992).
Harris et al., "Efficacy of acemannan in treatment of canine and feline spontaneous neoplasms" *Mol. Biother.* 3:207–213 Dec. (1991).
Garnett, P.B., "Immunostimulant Brings Positive Results in Studies" *Veterinary Forum* (Mar. 1993).
Peng et al., "Decreased mortality of Norman Murine Sarcoma in mice treated with the immunomodulator, Acemannan" *Mol. Biother.* 3:79–87 (Jun. 1991).
Rodriguez–Bigas et al., "Comparative Evaluation of Aloe Vera in the Management of Burn Wounds in Guinea Pigs" *Plastic and Reconstructive Surgery* 81(3):386–389 (Mar. 1988).
Swaim et al., "Effects of Topical Medications on the Healing of Open Pad Wounds in Dogs" *Journal of the American Animal Hospital Association* 28:499–502 (Nov./Dec. 1992).
Niagro et al., "Avian Polyomavirus: Discordance Between Neutralizing Antibody Titers and Viral Shedding in an Aviary" *Proceedings Association of Avian Veterinarians* 22–26 (1991).
Epstein et al., "Not all potentially neutralizing, vaccine–induced antibodies to Epstein–Barr virus ensure protection of susceptible experimental animals" *Clin. Exp. Immunol.* 63:485–490 (1986).
Chinnah et al., "Antigen dependent adjuvant activity of a apolydispersed β–(1,4)–linked acetylated mannan (acemannan)" *Vaccine* 10(8)551–557 (1992).
Della–Porta et al., "An Experimental Inactivated Virus Vaccine Against Bovine Ephemeral Fever. 2. Do Neutralizing Antibodies Protect Against Infection?" *Veterinary Microbiology* 4:197–208 (1979).
Dykstra et al., "Investigations of budgerigar fledgling disease virus" *Am. J. Vet. Res.* 45 (9) :1883–1887 (1984).
Ritchie et al., "Efficacy of an Inactivated Avian Polyomavirus Vaccine" *J. Assoc. Avian Vet.* 7:187–192 (1993).
Rodgers et al., "Purification of Racombinant Budgerigar Fledgling Disease Virus VP1 Capsid Protein and its Ability for In Vitro Capsid Assembly" *Journal of Virology* 68(5):3386–3390 (1994).
Yeung, H.A., "The Antigenic Properties of Recombinant VP1 from Budgerigar Fledgling Disease Virus Expressed in *Escherichia Coli*" Dissertation Submited to the Graduate Faculty of the University of Gerogia in Partial Fulfillment of the Requirements for Degree (1993).

(List continued on next page.)

Primary Examiner—Phuong T. Bui
(74) Attorney, Agent, or Firm—Needle & Rosenberg, P.C.

(57) ABSTRACT

The invention provides a nucleic acid vaccine which is protective against avian polyomavirus infection in a bird which is classified as being a member of the *Psittaciformes* order comprising a nucleic acid vaccine vector comprising a suitable eukaryotic cis-acting transcription/translation regulatory sequence functionally linked to a nucleic acid encoding an immunogenic avian polyomarvirus polypeptide. Methods for preventing avian polyomarvirus infection in a bird classified as being a member of the *Psittaciformes* order, are also provided.

6 Claims, No Drawings

OTHER PUBLICATIONS

Rekvig et al., "Antibodies to Eukaryotic, including Autologous, Native DNA are Produced during BK Virus Infection, but not after Immunization with Non–Infectious BK DNA" *Scand. J. Immunol.* 36:487–495 (1992).

Fattaey et al., "Production and Characterzation of Monoclonal Antibodies to Budgerigar Fledging Disease Virus Major Capsid Protein $VP_1$" *Avian Diseases* 36:543–553, (1992).

Leavitt et al., "Polyoma Virus Major Capsid Protein, $VP_1$" *J. Biol. Chem.* 260(23):12803–12809, (1985).

Salunke et al, "Self–Assembly of Purified Polyomavirus Capsid Protein $VP_1$" *Cell*, 46:895–904, (1986).

Vogel and Sarver, "Nucleic Acid Vaccines" *Clin. Micro. Rev.*, 8(3):406–410, (1995).

Rott et al., "The Genome of Budgerigar Fledgling Disease Virus, an Avian Polyomavirus" *Virology*, 165:74–86, (1988).

Irwin et al., "Direct Injection of a Recombinant Retroviral Vector Induces Human Immunodeficiency Virus–Specific Immune Responses in Mice and Nonhuman Primates" *J. Virol.*, 68(8):5036–5044, (1994).

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
(A) LENGTH: 2178 base pairs
(B) TYPE: nucleic acid
(C) STRANDEDNESS: double
(D) TOPOLOGY: linear (ii) MOLECULE TYPE: Genomic DNA (xi) SEQUENCE DESCRIPTION: SEQ ID NO:1:

```
AAGGAGACAG TGTATGCGGC AGGCACTAGC ACGGCAAGCA CTTCTGTCCC TCCTTCACAG    60

CCTAACTCGC CTACCCCTAC TGCTACCACC CCTGAGGCTT CTCCTGCTGC TCCTACTACC   120

GAGTCCACCG AGACAACCGG CCCTAGCGTC GCGACTAACG CAACCGAACC GTCCGAATCG   180

CGGCCGGCTC GCTAAGTAGC TGCACTAAGG TATGGGAGCT ATCATTTCGG CTATAGCTGG   240

TCTGTTCGAA CTAGGAGCAT TGGGTGGCCT AGCAGTAGAT GCTGCCGTAA ATACAGCAGA   300

AATAGAAGCA TTCATAGGGG AATTGGTACT GCAGGACTTT AGCGTTGCTG AAATATTCGA   360

CGCTATAGAA ACAAGTGGTA TACCTTTAGC GAATACCGCT GTACCTGTTG CAGAGCTACA   420

GCAAACAGCA GCAACTTCCG GGTTGATTGG ACAGGCGCTA AGTGCCCCAT CCCTGATAGC   480

GGCGTCAGTC AAGGCCTTTG CAGGAGACCC CGTCGCAGCC GGCAACAATA TGGCCCTACA   540

GGTCTGGAGA GACCAAATGG ACATACTCTT TCCAGGAGCG GAATGGTTCT CGAATGCTGT   600

ACATAATATC AATCCATTAG CATGGGCCCA ATCGTTGTAT GAACAAGTAG GCCAAAGTAT   660

ATGGAACTAT ATGACAGGTA ACATTGGGCA AGCTGTAATA CATCAAATCG AGGAGCGTAC   720

AACAGCCCTG ATTGTGTACC AAAGTAGGGG TATATATGAT ATACTTGCTA GAGCGTTAGA   780

AACCGCACGT TGGACATTAA CAACAGCGGC CGTAGATACA TATCAGACAC TAAAAAGCTA   840

CTATGGTGAG CTACCGGCTG TGTCGGGCAG AGTTGAGGCC TTTCGTAGGT ATCACGAGGT   900

CGCACAAGGA CGTAGCTTCT TTGAGGACTC AGATATACAA GATGTATTAG AGGGTAAAAA   960

GGCCCAAAAA CGAATTGAGG GCCCACAGGA GATGACAGGC CAAACCATAG AACAGCAAAC  1020

CCCCCCAGGA GGTGCAATGC AACGACATGC AAATGACTGG TTACTCCCTT TGATTCTAGG  1080

TCTCTACGGG GACCTGACTC CAGAGTGGCG GTACCAGCTT AAGGAAAGGC TCAATGTCCC  1140

AAAAAGGAAA AGGAAGCTGC CCACGACCTC AGCAGGTACC TCGCCTCCTA GTAAAAGGAG  1200

GTATAGAGGT GTTAGACGTA AAGTCAGGTC CAGATAGTAT AACAACCATA GAGGCATACC  1260

TTCAACCGCG GCCTGGACAA AAAAATGGAT ACTCCACAGT AATAACAGTG CAGGCAGAAG  1320

GATACCAGGA TGCCCCCCAC AGCACAGAGG TACCGTGTTA CAGCTGTGCC AGGATACCGC  1380

TCCCCACGAT CAACGACGAC ATTACGTGCC CGACCCTGCT TATGTGGGAG GCTGTCAGTG  1440
```

```
TTAAAACTGA GGTTGTTGGA GTGTCTAGTA TTCTCAACAT GCATTCTGGG GCTTTCCGCG   1500

CATTTAACGG ATACGGGGGA GGCTTTACTA TTTGTGGCCC TAGGATCCAT TTCTTTAGCG   1560

TGGGTGGAGA GCCTCTCGAT TTACAGGCAT GTATGCAAAA TTCAAAAACT GTGTACCCTG   1620

CACCCCTAAT TGGGCCTGGG GAAGGAGAAC GACGTGAAAC AGCACAGGTT CTCGATACGG   1680

GCTACAAGGC CCGACTAGAT AAGGATGGTC TCTACCCCAT TGAGTGCTGG TGCCCAGACC   1740

CTGCTAAGAA TGAGAACACT AGATATTATG CAACCTCAC AGGTGGGCCT GAGACCCCCC   1800

CTGTACTTGC CTTCACAAAC ACTACAACGA CAATTCTCCT TGATGAAAAT GGGGTTGGAC   1860

CCCTATGCAA GGGCGATGGC TTGTTCCTCT CAGCTGCAGA TGTGGCAGGT ACCTACGTTG   1920

ACCAACGTGG CCGCCAATAT TGGCGAGGCC TACCACGCTA TTTCAGTATC CAGCTGAGGA   1980

AACGTAATGT TCGTAACCCC TATCCTGTAT CTGGTTTGCT AAACTCCTTG TTCAATGACC   2040

TGATGCCCCG TATGACTGGT CAAAGCATGC AGGGCTCTGA TGCACAGGTG GAGGAGGTTC   2100

GTGTGTATGA GGGTATGGAA GGGCTGGCTC CCGAGATTGA CATGCCCCCC AAAGCTCCCC   2160

GCTAAATAGA CTAGACGC                                                 2178

(2) INFORMATION FOR SEQ ID NO:2:

(i) SEQUENCE CHARACTERISTICS:
        (A) LENGTH: 1973 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:2:

TGCACTAAGG TATGGGAGCT ATCATTTCGG CTATAGCTGG TCTGTTCGAA CTAGGAGCAT    60

TGGGTGGCCT AGCAGTAGAT GCTGCCGTAA ATACAGCAGA AATAGAAGCA TTCATAGGGG   120

AATTGGTACT GCAGGACTTT AGCGTTGCTG AAATATTCGA CGCTATAGAA ACAAGTGGTA   180

TACCTTTAGC GAATACCGCT GTACCTGTTG CAGAGCTACA GCAAACAGCA GCAACTTCCG   240

GGTTGATTGG ACAGGCGCTA AGTGCCCCAT CCCTGATAGC GGCGTCAGTC AAGGCCTTTG   300

CAGGAGACCC CGTCGCAGCC GGCAACAATA TGGCCCTACA GGTCTGGAGA GACCAAATGG   360

ACATACTCTT TCCAGGAGCG GAATGGTTCT CGAATGCTGT ACATAATATC AATCCATTAG   420

CATGGGCCCA ATCGTTGTAT GAACAAGTAG GCCAAAGTAT ATGGAACTAT ATGACAGGTA   480

ACATTGGGCA AGCTGTAATA CATCAAATCG AGGAGCGTAC AACAGCCCTG ATTGTGTACC   540

AAAGTAGGGG TATATATGAT ATACTTGCTA GAGCGTTAGA AACCGCACGT TGGACATTAA   600

CAACAGCGGC CGTAGATACA TATCAGACAC TAAAAAGCTA CTATGGTGAG CTACCGGCTG   660

TGTCGGGCAG AGTTGAGGCC TTTCGTAGGT ATCACGAGGT CGCACAAGGA CGTAGCTTCT   720

TTGAGGACTC AGATATACAA GATGTATTAG AGGGTAAAAA GGCCCAAAAA CGAATTGAGG   780

GCCCACAGGA GATGACAGGC CAAACCATAG AACAGCAAAC CCCCCCAGGA GGTGCAATGC   840

AACGACATGC AAATGACTGG TTACTCCCTT TGATTCTAGG TCTCTACGGG GACCTGACTC   900

CAGAGTGGCG GTACCAGCTT AAGGAAAGGC TCAATGTCCC AAAAAGGAAA AGGAAGCTGC   960

CCACGACCTC AGCAGGTACC TCGCCTCCTA GTAAAAGGAG GTATAGAGGT GTTAGACGTA  1020

AAGTCAGGTC CAGATAGTAT AACAACCATA GAGGCATACC TTCAACCGCG GCCTGGACAA  1080

AAAAATGGAT ACTCCACAGT AATAACAGTG CAGGCAGAAG GATACCAGGA TGCCCCCCAC  1140

AGCACAGAGG TACCGTGTTA CAGCTGTGCC AGGATACCGC TCCCCACGAT CAACGACGAC  1200
```

-continued

```
ATTACGTGCC CGACCCTGCT TATGTGGGAG GCTGTCAGTG TTAAAACTGA GGTTGTTGGA    1260

GTGTCTAGTA TTCTCAACAT GCATTCTGGG GCTTTCCGCG CATTTAACGG ATACGGGGGA    1320

GGCTTTACTA TTTGTGGCCC TAGGATCCAT TTCTTTAGCG TGGGTGGAGA GCCTCTCGAT    1380

TTACAGGCAT GTATGCAAAA TTCAAAAACT GTGTACCCTG CACCCCTAAT TGGGCCTGGG    1440

GAAGGAGAAC GACGTGAAAC AGCACAGGTT CTCGATACGG GCTACAAGGC CCGACTAGAT    1500

AAGGATGGTC TCTACCCCAT TGAGTGCTGG TGCCCAGACC CTGCTAAGAA TGAGAACACT    1560

AGATATTATG GCAACCTCAC AGGTGGGCCT GAGACCCCCC CTGTACTTGC CTTCACAAAC    1620

ACTACAACGA CAATTCTCCT TGATGAAAAT GGGGTTGGAC CCCTATGCAA GGGCGATGGC    1680

TTGTTCCTCT CAGCTGCAGA TGTGGCAGGT ACCTACGTTG ACCAACGTGG CCGCCAATAT    1740

TGGCGAGGCC TACCACGCTA TTTCAGTATC CAGCTGAGGA ACGTAATGT TCGTAACCCC     1800

TATCCTGTAT CTGGTTTGCT AAACTCCTTG TTCAATGACC TGATGCCCCG TATGACTGGT    1860

CAAAGCATGC AGGGCTCTGA TGCACAGGTG GAGGAGGTTC GTGTGTATGA GGGTATGGAA    1920

GGGCTGGCTC CCGAGATTGA CATGCCCCCC AAAGCTCCCC GCTAAATAGA CTA           1973
```

(2) INFORMATION FOR SEQ ID NO:3:

(i) SEQUENCE CHARACTERISTICS:
        (A) LENGTH: 1023 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:3:

```
ATGGGAGCTA TCATTTCGGC TATAGCTGGT CTGTTCGAAC TAGGAGCATT GGGTGGCCTA      60

GCAGTAGATG CTGCCGTAAA TACAGCAGAA ATAGAAGCAT TCATAGGGGA ATTGGTACTG     120

CAGGACTTTA GCGTTGCTGA AATATTCGAC GCTATAGAAA CAAGTGGTAT ACCTTTAGCG     180

AATACCGCTG TACCTGTTGC AGAGCTACAG CAAACAGCAG CAACTTCCGG GTTGATTGGA     240

CAGGCGCTAA GTGCCCCATC CCTGATAGCG GCGTCAGTCA AGGCCTTTGC AGGAGACCCC     300

GTCGCAGCCG GCAACAATAT GGCCCTACAG GTCTGGAGAG ACCAAATGGA CATACTCTTT     360

CCAGGAGCGG AATGGTTCTC GAATGCTGTA CATAATATCA ATCCATTAGC ATGGGCCCAA     420

TCGTTGTATG AACAAGTAGG CCAAAGTATA TGGAACTATA TGACAGGTAA CATTGGGCAA     480

GCTGTAATAC ATCAAATCGA GGAGCGTACA ACAGCCCTGA TTGTGTACCA AGTAGGGGT     540

ATATATGATA TACTTGCTAG AGCGTTAGAA ACCGCACGTT GGACATTAAC AACAGCGGCC     600

GTAGATACAT ATCAGACACT AAAAAGCTAC TATGGTGAGC TACCGGCTGT GTCGGGCAGA     660

GTTGAGGCCT TTCGTAGGTA TCACGAGGTC GCACAAGGAC GTAGCTTCTT TGAGGACTCA     720

GATATACAAG ATGTATTAGA GGGTAAAAAG GCCCAAAAAC GAATTGAGGG CCCACAGGAG     780

ATGACAGGCC AAACCATAGA ACAGCAAACC CCCCCAGGAG GTGCAATGCA ACGACATGCA     840

AATGACTGGT TACTCCCTTT GATTCTAGGT CTCTACGGGG ACCTGACTCC AGAGTGGCGG     900

TACCAGCTTA AGGAAAGGCT CAATGTCCCA AAAAGGAAAA GGAAGCTGCC CACGACCTCA     960

GCAGGTACCT CGCCTCCTAG TAAAAGGAGG TATAGAGGTG TTAGACGTAA AGTCAGGTCC    1020

AGA                                                                 1023
```

(2) INFORMATION FOR SEQ ID NO:4:

-continued (i) SEQUENCE CHARACTERISTICS:
    (A) LENGTH: 341 amino acids
    (B) TYPE: amino acid
    (C) STRANDEDNESS: single
    (D) TOPOLOGY: linear (ii) MOLECULE TYPE: protein (ix) FEATURE:
    (D) OTHER INFORMATION: VP2 protein (xi) SEQUENCE DESCRIPTION: SEQ ID NO:4:

```
Met Gly Ala Ile Ile Ser Ala Ile Ala Gly Leu Phe Glu Leu Gly Ala
 1               5                  10                  15

Leu Gly Gly Leu Ala Val Asp Ala Ala Val Asn Thr Ala Glu Ile Glu
                20                  25                  30

Ala Phe Ile Gly Glu Leu Val Leu Gln Asp Phe Ser Val Ala Glu Ile
            35                  40                  45

Phe Asp Ala Ile Glu Thr Ser Gly Ile Pro Leu Ala Asn Thr Ala Val
50                  55                  60

Pro Val Ala Glu Leu Gln Gln Thr Ala Ala Thr Ser Gly Leu Ile Gly
65                  70                  75                  80

Gln Ala Leu Ser Ala Pro Ser Leu Ile Ala Ala Ser Val Lys Ala Phe
                85                  90                  95

Ala Gly Asp Pro Val Ala Ala Gly Asn Asn Met Ala Leu Gln Val Trp
            100                 105                 110

Arg Asp Gln Met Asp Ile Leu Phe Pro Gly Ala Glu Trp Phe Ser Asn
            115                 120                 125

Ala Val His Asn Ile Asn Pro Leu Ala Trp Ala Gln Ser Leu Tyr Glu
        130                 135                 140

Gln Val Gly Gln Ser Ile Trp Asn Tyr Met Thr Gly Asn Ile Gly Gln
145                 150                 155                 160

Ala Val Ile His Gln Ile Glu Glu Arg Thr Thr Ala Leu Ile Val Tyr
                165                 170                 175

Gln Ser Arg Gly Ile Tyr Asp Ile Leu Ala Arg Ala Leu Glu Thr Ala
            180                 185                 190

Arg Trp Thr Leu Thr Thr Ala Ala Val Asp Thr Tyr Gln Thr Leu Lys
        195                 200                 205

Ser Tyr Tyr Gly Glu Leu Pro Ala Val Ser Gly Arg Val Glu Ala Phe
        210                 215                 220

Arg Arg Tyr His Glu Val Ala Gln Gly Arg Ser Phe Phe Glu Asp Ser
225                 230                 235                 240

Asp Ile Gln Asp Val Leu Glu Gly Lys Lys Ala Gln Lys Arg Ile Glu
                245                 250                 255

Gly Pro Gln Glu Met Thr Gly Gln Thr Ile Glu Gln Gln Thr Pro Pro
            260                 265                 270

Gly Gly Ala Met Gln Arg His Ala Asn Asp Trp Leu Leu Pro Leu Ile
        275                 280                 285

Leu Gly Leu Tyr Gly Asp Leu Thr Pro Glu Trp Arg Tyr Gln Leu Lys
        290                 295                 300

Glu Arg Leu Asn Val Pro Lys Arg Lys Arg Lys Leu Pro Thr Thr Ser
305                 310                 315                 320

Ala Gly Thr Ser Pro Pro Ser Lys Arg Arg Tyr Arg Gly Val Arg Arg
                325                 330                 335

Lys Val Arg Ser Arg
            340
```

(2) INFORMATION FOR SEQ ID NO:5:

(i) SEQUENCE CHARACTERISTICS:
        (A) LENGTH: 705 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:5:

```
ATGGCCCTAC AGGTCTGGAG AGACCAAATG GACATACTCT TTCCAGGAGC GGAATGGTTC      60
TCGAATGCTG TACATAATAT CAATCCATTA GCATGGGCCC AATCGTTGTA TGAACAAGTA     120
GGCCAAAGTA TATGGAACTA TATGACAGGT AACATTGGGC AAGCTGTAAT ACATCAAATC     180
GAGGAGCGTA CAACAGCCCT GATTGTGTAC CAAAGTAGGG GTATATATGA TATACTTGCT     240
AGAGCGTTAG AAACCGCACG TTGGACATTA ACAACAGCGG CCGTAGATAC ATATCAGACA     300
CTAAAAAGCT ACTATGGTGA GCTACCGGCT GTGTCGGGCA GAGTTGAGGC CTTTCGTAGG     360
TATCACGAGG TCGCACAAGG ACGTAGCTTC TTTGAGGACT CAGATATACA AGATGTATTA     420
GAGGGTAAAA AGGCCCAAAA ACGAATTGAG GGCCCACAGG AGATGACAGG CCAAACCATA     480
GAACAGCAAA CCCCCCCAGG AGGTGCAATG CAACGACATG CAAATGACTG GTTACTCCCT     540
TTGATTCTAG GTCTCTACGG GGACCTGACT CCAGAGTGGC GGTACCAGCT TAAGGAAAGG     600
CTCAATGTCC CAAAAAGGAA AAGGAAGCTG CCCACGACCT CAGCAGGTAC CTCGCCTCCT     660
AGTAAAAGGA GGTATAGAGG TGTTAGACGT AAAGTCAGGT CCAGA                     705
```

(2) INFORMATION FOR SEQ ID NO:6:

(i) SEQUENCE CHARACTERISTICS:
        (A) LENGTH: 235 amino acids
        (B) TYPE: amino acid
        (C) STRANDEDNESS: single
        (D) TOPOLOGY: linear (ii) MOLECULE TYPE: protein (ix) FEATURE:
        (D) OTHER INFORMATION: VP3 protein (xi) SEQUENCE DESCRIPTION: SEQ ID NO:6:

```
Met Ala Leu Gln Val Trp Arg Asp Gln Met Asp Ile Leu Phe Pro Gly
 1               5                  10                  15

Ala Glu Trp Phe Ser Asn Ala Val His Asn Ile Asn Pro Leu Ala Trp
                20                  25                  30

Ala Gln Ser Leu Tyr Glu Gln Val Gly Gln Ser Ile Trp Asn Tyr Met
            35                  40                  45

Thr Gly Asn Ile Gly Gln Ala Val Ile His Gln Ile Glu Glu Arg Thr
        50                  55                  60

Thr Ala Leu Ile Val Tyr Gln Ser Arg Gly Ile Tyr Asp Ile Leu Ala
65                  70                  75                  80

Arg Ala Leu Glu Thr Ala Arg Trp Thr Leu Thr Thr Ala Ala Val Asp
                85                  90                  95

Thr Tyr Gln Thr Leu Lys Ser Tyr Tyr Gly Glu Leu Pro Ala Val Ser
            100                 105                 110

Gly Arg Val Glu Ala Phe Arg Arg Tyr His Glu Val Ala Gln Gly Arg
        115                 120                 125

Ser Phe Phe Glu Asp Ser Asp Ile Gln Asp Val Leu Glu Gly Lys Lys
    130                 135                 140
```

Ala Gln Lys Arg Ile Glu Gly Pro Gln Glu Met Thr Gly Gln Thr Ile
145                 150                 155                 160

Glu Gln Gln Thr Pro Pro Gly Gly Ala Met Gln Arg His Ala Asn Asp
                165                 170                 175

Trp Leu Leu Pro Leu Ile Leu Gly Leu Tyr Gly Asp Leu Thr Pro Glu
            180                 185                 190

Trp Arg Tyr Gln Leu Lys Glu Arg Leu Asn Val Pro Lys Arg Lys Arg
        195                 200                 205

Lys Leu Pro Thr Thr Ser Ala Gly Thr Ser Pro Pro Ser Lys Arg Arg
    210                 215                 220

Tyr Arg Gly Val Arg Arg Lys Val Arg Ser Arg
225                 230                 235

(2) INFORMATION FOR SEQ ID NO:7:

(i) SEQUENCE CHARACTERISTICS:
        (A) LENGTH: 1029 base pairs
        (B) TYPE: nucleic acid
        (C) STRANDEDNESS: double
        (D) TOPOLOGY: linear (ii) MOLECULE TYPE: Genomic DNA (xi) SEQUENCE DESCRIPTION: SEQ ID NO:7:

ATGTCCCAAA AAGGAAAAGG AAGCTGCCCA CGACCTCAGC AGGTACCTCG CCTCCTAGTA      60

AAAGGAGGTA TAGAGGTGTT AGACGTAAAG TCAGGTCCAG ATAGTATAAC AACCATAGAG     120

GCATACCTTC AACCGCGGCC TGGACAAAAA AATGGATACT CCACAGTAAT AACAGTGCAG     180

GCAGAAGGAT ACCAGGATGC CCCCCACAGC ACAGAGGTAC CGTGTTACAG CTGTGCCAGG     240

ATACCGCTCC CCACGATCAA CGACGACATT ACGTGCCCGA CCCTGCTTAT GTGGGAGGCT     300

GTCAGTGTTA AAACTGAGGT TGTTGGAGTG TCTAGTATTC TCAACATGCA TTCTGGGGCT     360

TTCCGCGCAT TTAACGGATA CGGGGGAGGC TTTACTATTT GTGGCCCTAG GATCCATTTC     420

TTTAGCGTGG GTGGAGAGCC TCTCGATTTA CAGGCATGTA TGCAAAATTC AAAAACTGTG     480

TACCCTGCAC CCCTAATTGG GCCTGGGGAA GGAGAACGAC GTGAAACAGC ACAGGTTCTC     540

GATACGGGCT ACAAGGCCCG ACTAGATAAG GATGGTCTCT ACCCCATTGA GTGCTGGTGC     600

CCAGACCCTG CTAAGAATGA GAACACTAGA TATTATGGCA ACCTCACAGG TGGGCCTGAG     660

ACCCCCCCTG TACTTGCCTT CACAAACACT ACAACGACAA TTCTCCTTGA TGAAAATGGG     720

GTTGGACCCC TATGCAAGGG CGATGGCTTG TTCCTCTCAG CTGCAGATGT GGCAGGTACC     780

TACGTTGACC AACGTGGCCG CCAATATTGG CGAGGCCTAC CACGCTATTT CAGTATCCAG     840

CTGAGGAAAC GTAATGTTCG TAACCCCTAT CCTGTATCTG GTTTGCTAAA CTCCTTGTTC     900

AATGACCTGA TGCCCCGTAT GACTGGTCAA AGCATGCAGG CTCTGATGC ACAGGTGGAG      960

GAGGTTCGTG TGTATGAGGG TATGGAAGGG CTGGCTCCCG AGATTGACAT GCCCCCCAAA    1020

GCTCCCCGC                                                            1029

(2) INFORMATION FOR SEQ ID NO:8:

(i) SEQUENCE CHARACTERISTICS:
        (A) LENGTH: 343 amino acids
        (B) TYPE: amino acid
        (C) STRANDEDNESS: single
        (D) TOPOLOGY: linear (ii) MOLECULE TYPE: protein (ix) FEATURE:
        (D) OTHER INFORMATION: VP1 protein (xi) SEQUENCE DESCRIPTION: SEQ ID NO:8:

Met Ser Gln Lys Gly Lys Gly Ser Cys Pro Arg Pro Gln Gln Val Pro
1               5                   10                  15

Arg Leu Leu Val Lys Gly Gly Ile Glu Val Leu Asp Val Lys Ser Gly
                20                  25                  30

Pro Asp Ser Ile Thr Thr Ile Glu Ala Tyr Leu Gln Pro Arg Pro Gly
                35                  40                  45

Gln Lys Asn Gly Tyr Ser Thr Val Ile Thr Val Gln Ala Glu Gly Tyr
50                          55                  60

Gln Asp Ala Pro His Ser Thr Glu Val Pro Cys Tyr Ser Cys Ala Arg
65                  70                  75                  80

Ile Pro Leu Pro Thr Ile Asn Asp Asp Ile Thr Cys Pro Thr Leu Leu
                85                  90                  95

Met Trp Glu Ala Val Ser Val Lys Thr Glu Val Val Gly Val Ser Ser
                100                 105                 110

Ile Leu Asn Met His Ser Gly Ala Phe Arg Ala Phe Asn Gly Tyr Gly
                115                 120                 125

Gly Gly Phe Thr Ile Cys Gly Pro Arg Ile His Phe Phe Ser Val Gly
        130                 135                 140

Gly Glu Pro Leu Asp Leu Gln Ala Cys Met Gln Asn Ser Lys Thr Val
145                 150                 155                 160

Tyr Pro Ala Pro Leu Ile Gly Pro Gly Glu Gly Arg Arg Glu Thr
                165                 170                 175

Ala Gln Val Leu Asp Thr Gly Tyr Lys Ala Arg Leu Asp Lys Asp Gly
                180                 185                 190

Leu Tyr Pro Ile Glu Cys Trp Cys Pro Asp Pro Ala Lys Asn Glu Asn
        195                 200                 205

Thr Arg Tyr Tyr Gly Asn Leu Thr Gly Gly Pro Glu Thr Pro Pro Val
        210                 215                 220

Leu Ala Phe Thr Asn Thr Thr Thr Ile Leu Leu Asp Glu Asn Gly
225                 230                 235                 240

Val Gly Pro Leu Cys Lys Gly Asp Gly Leu Phe Leu Ser Ala Ala Asp
                245                 250                 255

Val Ala Gly Thr Tyr Val Asp Gln Arg Gly Arg Gln Tyr Trp Arg Gly
                260                 265                 270

Leu Pro Arg Tyr Phe Ser Ile Gln Leu Arg Lys Arg Asn Val Arg Asn
        275                 280                 285

Pro Tyr Pro Val Ser Gly Leu Leu Asn Ser Leu Phe Asn Asp Leu Met
290                 295                 300

Pro Arg Met Thr Gly Gln Ser Met Gln Gly Ser Asp Ala Gln Val Glu
305                 310                 315                 320

Glu Val Arg Val Tyr Glu Gly Met Glu Gly Leu Ala Pro Glu Ile Asp
                325                 330                 335

Met Pro Pro Lys Ala Pro Arg
                340

(2) INFORMATION FOR SEQ ID NO:9:

(i) SEQUENCE CHARACTERISTICS:
        (A) LENGTH: 183 base pairs
        (B) TYPE: nucleic acid
        (C) STRANDEDNESS: double
        (D) TOPOLOGY: linear -continued

```
    (ii) MOLECULE TYPE: Genomic DNA (xi) SEQUENCE DESCRIPTION: SEQ ID NO:9:

ATGCGGCAGG CACTAGCACG GCAAGCACTT CTGTCCCTCC TTCACAGCCT AACTCGCCTA    60

CCCCTACTGC TACCACCCCT GAGGCTTCTC CTGCTGCTCC TACTACCGAG TCCACCGAGA   120

CAACCGGCCC TAGCGTCGCG ACTAACGCAA CCGAACCGTC CGAATCGCGG CCGGCTCGCT   180

AAG                                                                 183

(2) INFORMATION FOR SEQ ID NO:10:

(i) SEQUENCE CHARACTERISTICS:
          (A) LENGTH: 61 amino acids
          (B) TYPE: amino acid
          (C) STRANDEDNESS: single
          (D) TOPOLOGY: linear (ii) MOLECULE TYPE: protein (ix) FEATURE:
          (D) OTHER INFORMATION: Agno Amino Acid Sequence (xi) SEQUENCE DESCRIPTION: SEQ ID NO:10:

Met Arg Gln Ala Leu Ala Arg Gln Ala Leu Leu Ser Leu Leu His Ser
 1               5                  10                  15

Leu Thr Arg Leu Pro Leu Leu Leu Pro Pro Leu Arg Leu Leu Leu Leu
            20                  25                  30

Leu Leu Leu Pro Ser Pro Pro Arg Gln Pro Ala Leu Ala Ser Arg Leu
        35                  40                  45

Thr Gln Pro Asn Arg Pro Asn Arg Gly Arg Leu Ala Lys
    50                  55                  60
```

AVIAN POLYOMAVIRUS VACCINES IN PSITTACINE BIRDS

This application is a continuation-in-part of Ser. No. 08/660,227, which was filed on Jun. 3, 1996, "now issued as U.S. Pat. No. 5,747,045, which is a Continuation-In-Part of Ser. No. 08/180,929, filed on Jan. 13, 1994, now issued as U.S. Pat. No. 5,523,088".

BACKGROUND OF THE INVENTION

1. Field of the Invention

The present invention relates to an avian polyomavirus vaccine and to a method of preventing avian polyomavirus infection in *Psittaciformes*.

2. Background Art

The first acute, generalized infection associated with avian polyomavirus was described in 1980 in young psittacine birds and was called budgerigar fledgling disease (Davis, R. R. et al., "A viral disease of fledgling budgerigars," *Avian Dis.*, 1981, 25:179–183; Bozeman, L. H., et al., "Characterization of a papovavirus isolated from fledgling budgerigars," *Avian Dis.*, 1981, 25:972–980; Bernier, G., et al., "A generalized inclusion body disease in the budgerigar (*Melopsittacus undulatus*) caused by a papovavirus-like agent," *Avian Dis.*, 1981, 25:1083–1092; Dykstra, M. J., et al., "Investigations of budgerigar fledgling disease virus," *Am. J. Vet. Res.*, 1984, 45:1883–1887; Lehn, H., Muller, H., "Cloning and characterization of budgerigar fledgling disease virus (BFDV), an avian polyomavirus," *Virology*, 1986, 151:362–370). Since its discovery in 1980, avian polyomavirus has been associated with disease in a number of different species of companion and aviary birds including Budgerigars, caiques, macaws, Amazon parrots, conures, cockatoos, lovebirds, Splendid Parakeet, Pionus Parrots, African Grey Parrots, Eclectus Parrots, Cockatiels, finches and lories (Davies et al., 1981; Bozeman et al., 1981; Bernier et al., 1981; Lehn and Muller, 1986; Jacobson, E. R., et al., "Epornitic of papova-like virus-associated disease in a psittacine nursery," *J. Am. Vet. Med. Assoc.*, 1984, 185:1337–1341; Clubb, S. L., Davis, R. B., "Outbreak of papova-like viral infection in a psittacine nursery-a retrospective view," *Proc. Assoc. Avian Vet.*, Toronto, 1984, 121–129; Graham, D. L., "An update on selected pet bird virus infections," *Proc. Assoc. Avian Vet.*, Toronto, 1984, 267–280; Gaskin, J. M., "Psittacine viral disease: A perspective," *J. Zoo. Wildl. Med.*, 1989, 20:240–264; Johnston, K. M., Riddell, C., "Intranuclear inclusion bodies in finches," *Can. Vet. J.*, 1986, 27:432–434; Marshall, R., "Papova-like virus in a finch aviary, *Proc. Assoc. Avian Vet.*, 1989, 203–207; Schmidt, R. E., et al., "Morphologic identification of papovavirus in a Moluccan cockatoo (*Cacatua moluceensis*) with neurologic signs," *Assoc. Avian Vet. Today*, 1987, 1:107–108; Pass, D. A., et al., "A papova-like virus infection of splendid parakeets (*Neophema splendida*)," *Avian Dis.*, 1987, 31:680–684; Pass, D. A., "A papova-like virus infection of lovebirds (*Agapornis sp.*(," *Aus. Vet. J.;* 1985, 82:318–319).

The type of clinical disease in Budgerigars, for example, depends upon the age and condition of birds when exposure to the virus occurs. Neonates from infected flocks may develop normally for 10–15 days and then suddenly die with no premonitory signs. Other infected hatchlings may develop clinical signs that include abdominal distention, subcutaneous hemorrhage, tremors of the head and neck, ataxia and reduced formation of down and contour feathers feather abnormalities," *J. Vet. Sci.* 46:577–587, 1984; Bernier et al., 1984; Clubb and Davis, 1984; Schmidt et al., 1987; Histopathology Reports #SC90-0637 and #SC90-0638, Schubot Exotic Bird health Center, Texas A&M University; Vernot, J., personal communication; Dykstra, M. J., Bozeman, L. H., "A light and electron microscopic examination of budgerigar fledgling disease virus in tissue and in cell culture. *Avian Pathol.* 11:11–18, 1982). Infections have also been associated with decreased hatchability and embryonic death (Hudson, L., Hay, F. C., "Isolation and structure of immunoglobulins," Hudson, L., Hay, F. C. Ed., *Practical Immunology*, Boston, 1980, 156–202). Mortality rates can be as high as 100% in affected hatchlings. Surviving birds often exhibit dystrophic primary tail feathers, lack of down feathers on the back and abdomen, and lock of filoplumes on the head and neck. Additionally, surviving birds with primary feather abnormalities are usually unable to fly.

In larger psittacine birds, polyomavirus infections may cause peracute death with no premonitory signs, or acute death after development of clinical changes including depression, anorexia, weight loss, delayed crop-emptying, regurgitation, diarrhea, dehydration, subcutaneous hemorrhages, dyspnea, polyuria, and posterior paresis and paralysis (Pass et al., 1987; Johnston and Riddell, 1986; Mathey, W. J., Cho, B. R., "Tremors of nestling budgerigars with budgerigar fledgling disease," *Proc. 33rd West Poult. Dis. Conf.*, 1984, 102; Woods, L., "Papova-like virus in a purple finch," *J. Zoo. Wildl. Med.*, 1989, 218–218; Gaskin, J. M., "The serodiagnosis of psittacine viral infections," *Assoc. Avian Vet.* Honolulu, 1988, 7–10). Characteristic lesions associated with a polyomavirus infection have been demonstrated in companion birds from the United States (Jacobson et al., 1984; Clubb and Davis, 1984; Graham, 1984), Canada (Gough, J. F., "Outbreaks of budgerigar fledgling disease in three aviaries in Ontario,: *Can. Vet. J.*, 1989, 30:672–674, Bernier et al., 1984), Japan (Hirai et al., 1984), Italy (Pascucci, S., et al., "Malattia da virus papovasimile nel papagallino ondulato (*Melopsittacus undulatus*), *Clin. Med.* (*Milan*), 1983, 106:38–41), Hungary (Szotjkov, V., et al., "A hullamous papagaj (*Melopsittacus Undulatus*) papovavirus okozta megbetegedesenek hazai megallapitasa, *Magy Allatorv Lapja* 1985, 40:50–63), Germany (Krautwald, M–E, Kaleta, E. F., "Relationship of French moult and early virus induced mortality in nestling budgerigars," *Proc. 8th Intl. Cong. World Vet. Poult. Assoc.*, 1985, 115) and Australia (Pass et al., 1987; Pass, 1985).

Immunodiffusion and virus neutralization techniques have been used to demonstrate anti-polyomavirus antibodies in psittacine birds (Jacobson et al., 1984; Clubb and Davis, 1984; Gaskin, 1989; Davis et al., 1981; Gaskin, 1988; Lynch, J., et al., "Isolation and experimental chicken-embryo-inoculation studies with budgerigar papovavirus," *Avian Dis.* 1984, 28:1135–1139; Wainwright, P. O., et al., "Serological evaluation of some psittaciformes for budgerigar fledgling disease virus," *Avian Dis.* 1987, 31:673–676). During epornitics in mixed psittacine bird collection, infected survivors and asymptomatic birds exposed to them have been shown to develop anti-polyomavirus neutralizing antibodies (Jacobson et al., 1984; Clubb and Davis, 1984; Wainwright et al., 1987). Seronegative young adult birds will seroconvert when housed adjacent to seropositive breeding adults; indicating that an antibody response does occur following natural exposure to the virus (Jacobson et al., 1984; Clubb and Davis, 1984; Wainwright et al., 1987; Davis, R. B., "Budgerigar fledgling disease (BFD), 32*nd* West Poult. Dis. Conf., 1983, 104). However, prior to the present invention it had not been determined whether this antibody response could be induced through vaccination or whether the resulting immunologic response would be protective.

In the past, attempts at producing a vaccine against avian polyomavirus have been unsuccessful. The existence of subclinical infections and chronically infected carrier birds, coupled with a lack of understanding of the epidemiologic and pathophysiologic characteristics of infection have all contributed to the lack of success.

Consequently, avian polyomavirus infections continue to cause high levels of mortality in companion and aviary birds, resulting in pscyhological distress for clients and financial burdens for aviculturists and retail distributors despite discovery of the virus over 14 years ago. Therefore, there exists a long-felt need in the art for a safe and effective vaccine against avian polyomavirus which is crossprotective against the disease in multiple species of *Psittaciformes*.

Another problem associated with vaccine failure in *Psittaciformes* has been the lack of a suitable adjuvant. Two killed oil-adjuvanted herpesvirus (Pacheco's disease virus) vaccines that were conditionally licensed for use in *Psittaciformes* were found to cause unacceptable reactions in a number of vaccinates, particularly cockatoos (Davis et al., 1981; Bozeman et al., 1981; Bernier et al., 1981; Dykstra et al., 1984). These reactions were characterized by the formation of abscesses (subcutaneous inoculation) or muscle necrosis (IM inoculation). In some *Psittaciformes*, granulomatous or necrotizing lesions were not noted until several months after vaccination. In other birds, lesions were noted within several weeks of administration of a booster vaccination (Davis et al., 1981; Bozeman et al., 1981; Schmidt et al., 1987). In some cases, deaths have been associated with the use of oil-adjuvanted vaccines.

In general, the advantage of oil-adjuvanted vaccines in comparison to other immunization products is their ability to induce durable immunity when mixed with an inactivated antigen. However, the occurrence of adverse reactions in some *Psittaciformes* vaccinated with oil-adjuvanted vaccines created the need for an alternative adjuvant for use with inactivated antigens intended for administration in this order of birds (Davis et al., 1981; Bozeman et al., 1981; Schmidt et al., 1987). Therefore, there exists a need in the art for a suitable adjuvant for use in *Psittaciformes* which augments the immune response yet does not produce an adverse reaction in the vaccinate.

SUMMARY OF THE INVENTION

The present invention satisfies the long-felt need in the art for a safe and effective vaccine to protect psittacine birds against avian polyomavirus disease by providing a vaccine which is protective against avian polyomavirus infection in a bird which is classified as being a member of the *Psittaciformes* order, comprising an immunogenic amount of an inactivated avian polyomavirus and a pharmaceutically acceptable carrier.

In one embodiment, the vaccine is derived from a strain of inactivated avian polyomavirus known as the L4 strain. In another embodiment, the invention provides a vaccine wherein immunogenic amount of the inactivated avian polyomavirus corresponds to a titer of between $10^{4.5} TCID_{50}$ and $10^{7} TCID_{50}$ for the avian polyomavirus before inactivation, but especially about $10^{5.8} TCID_{50}$.

The present invention also satisfies the need for a suitable adjuvant for use in psittacine species by providing an adjuvant, e.g., a long chain polydispersed beta- (1,4) linked mannan polymer interspersed with O-acetylated groups such as ACEMANNAN, (Carrington Laboratories, Dallas, Tx.) for use, not only in the vaccines of the present invention, but also in other psittacine vaccines.

Also provided is a composition which produces either a primary or an anamnestic response against avain polyomavirus infection in a sensitized bird which is classified as being a member of the *Psittaciformes* order, comprising a primary or an anamnestic response inducing amount of a recombinant protein of avian polyomavirus and a pharmaceutically acceptable carrier. In one embodiment, the composition comprises a recombinant VP1 capsid protein of avian polyomavirus.

In another embodiment, the recombinant protein is produced in the bird's cells by the injection of plasmids encoding the recombinant proteins. In a specific embodiment, the plasmid is constructed of nucleic acid sequences encoding the agnogene, VP2, VP3, and VP1 proteins of avian polyomavirus. Alternatively, the plasmid can be constructed without the agnogene sequence. In an alternative embodiment, the plasmid will encode one or more nucleic acid sequences from the group consisting of avian polyomavirus agnogene, VP1, VP2, and VP3 proteins.

The present invention also provides a method of preventing avian polyomavirus infection in a bird which is classified as being a member of the *Psittaciformes* order, comprising administering to the bird a vaccine comprising an immunogenic amount of an inactivated avian polyomavirus and a pharmaceutically acceptable carrier. In one embodiment, the method further comprises administering at least one booster vaccine to the bird.

Further, the invention provides a method of preventing avian polyomavirus infection in a bird from a species which is classified as being a member of the *Psittaciformes* order, comprising administering to the bird a vaccine comprising an immunogenic amount of an inactivated avian polyomavirus which infects a bird from a different species of the *Psittaciformes* order an a pharmaceutically acceptable carrier. The vaccines and compositions provided by the invention can be utilized in the methods provided herein.

DETAILED DESCRIPTION OF THE INVENTION

The present invention is more particularly described in the following examples which are intended as illustrative only since numerous modifications and variations therein will be apparent to those skilled in the art.

As used in the claims, "a" can mean one or more, depending on the context of the claim.

The present invention provides a vaccine which is protective against avian polyomavirus infection in a bird which is classified as being a member of the *Psittaciformes* order. One embodiment comprises an immunogenic amount of an inactivated avian polyomavirus and a pharmaceutically acceptable carrier. Another embodiment comprises a vaccine which is protective against avian polyomavirus infection in a bird which is classified as being a member of the *Psittaciformes* order, comprising an immunogenic amount of a recombinant protein derived from an avian polyomavirus and a pharmaceutically acceptable carrier.

The term "immunogenic amount" means an amount of an immunogen, i.e., the inactivated avian polyomavirus or a portion thereof, which is sufficient to induce an immune response in the vaccinated bird and which protects the bird against active infection with avian polyomavirus upon exposure thereto.

The terms "nucleic acid vaccine", "nucleic acid vaccine vector", and "naked nucleic acid vaccine", which are used interchangeably herein, mean a vaccine delivered in the form of a non-replicating nucleic acid.

The birds which can be treated by the invention can be any of the various species of birds which are classified as being members of the *Psittaciformes* order. Examples of such birds include, but are not limited to, Budgerigars (*Melopsittacus undulatus*), caiques (e.g., *Pionites leucogaster leucogaster*), macaws (e.g., *Ara ararauna*), Amazon parrots (e.g., *Amazona ochrocephala auropalliata*, courses (e.g., *Pyrrhara picta, Aratinga wagleri wagleri, Aratinga solstitialis, Aratinga guarouba, Artinga holochlora rubritorquis* or *Aratinga acuticaudata acuticaudata*), cockatoos (e.g., *Cacatua moluccensis, Cacatua ducorps, Cacatua sulphura, Cacatua goffini* or *Cacatua alba*), Splendid Parakeets (*Neophema splendid*), Pionus Parrots (*Pionus maximillani*), African Grey Parrots (*Psittacus erithacus erithacus*), Eclectus Parrots (*Electus roratus*), Cockatiels (*Nymphicus hollandicus*) and parakeets (e.g. *Psittacula krameri krameri*). Specifically exemplified by the invention is a vaccine which is protective against avian polyomavirus infection in a bird which is classified as being a member of the *Psittaciformes* order, comprising an immunogenic amount of an inactivated avian polyomavirus and a pharmaceutically acceptable carrier wherein the bird is selected from the group consisting of a macaw, an Amazon parrot, a conure, a cockatoo, a Pionus Parrot, and an African Grey Parrot.

Given the surprising fact provided by the invention that avian polyomavirus can be prevented in multiple species of *Psittaciformes* utilizing a single strain of avian polyomavirus, it is contemplated that the vaccines of the present invention can be constructed from any isolated strain of avian polyomavirus which infects a member of the *Psittaciformes* order by utilizing the methods taught herein. For example, the subject avian polyomavirus can be isolated and cultured utilizing the method taught by Bozeman et al., 1981 or by other methods known in the art. Once isolated, the virus can be purified if desired, inactivated, the vaccine prepared and the immunogenic dose optimized by the methods taught herein.

In one embodiment of the invention, the inactivated avian polyomavirus vaccine is derived from an isolated avian polyomavirus designated the "L4" strain. The L4 strain was isolated from an infected Budgerigar at the University of Georgia College of Veterinary Medicine in 1981 utilizing the method of Bozeman et al., 1981, and can be obtained from the Laboratory of Dr. Phil D. Lukert, College of Veterinary Medicine, University of Georgia, Athena, Ga. 30602.

One embodiment of the invention provides a vaccine which is protective against avian polyomavirus infection in a bird which is classified as being a member of the *Psittaciformes* order, comprising an immunogenic amount of an inactivated avian polyomavirus and a pharmaceutically acceptable carrier, wherein the immunogenic amount of the inactivated avian polyomavirus corresponds to a titer of between $10^{4.5}TCID_{50}$ and $10^{7}TCID_{50}$ for the avian polyomavirus before inactivation.

In a presently preferred embodiment, the immunogenic amount of the inactivated avian polyomavirus corresponds to a titer of $10^{5.8}TCID_{50}$ for the avian polyomavirus before inactivation. As used herein, the immunogenic amount is expressed in terms of "$TCID_{50}$" titer which is given its common meaning in the art of a tissue culture infection dose which infects 50% of the cells of a tissue culture inoculum. Thus, the immunogenic amount of any particular strain of inactivated avian polyomavirus that is utilized to prepare the vaccines of the invention is based upon the tissue culture infectivity titer for that particular strain of virus before the virus is inactivated for vaccine preparation. Also, depending upon the species, size and condition of the bird being vaccinated, the immunogenic amount can be varied by the optimization procedures taught herein or by procedures known in the art.

The vaccines of the present invention can be used either alone or in combination with a suitable adjuvant. In one embodiment the invention provides a vaccine which is protective against avian polyomavirus infection in a bird which is classified as being a member of the *Psittaciformes* order, comprising an immunogenic amount of an inactivated avian polyomavirus, a pharmaceutically acceptable carrier, and an adjuvant which is suitable for use in a bird which is classified as being a member of the *Psittaciformes* order. The term "suitable" is meant to include as an adjuvant, any substance which can be used in combination with the immunogen (e.g., inactivated avian polyomavirus or portion thereof) of the vaccine to augment the immune response without producing adverse side affects in the vaccinated bird. It is contemplated by the invention that the adjuvants described herein can be utilized in a vaccine against any psittacine pathogen. The adjuvants described herein can be utilized in any species which is a member of the *Psittaciformes* order including, but not limited to, the examples of *Psittaciformes* cited herein.

In one embodiment, the suitable adjuvant is a long chain polydispersed beta- (1,4) linked mannan polymer interspersed with O-acetylated groups. The presently preferred mannan polymer of the intention is ACEMANNAN. In another embodiment, the suitable adjuvant is a deproteinized highly purified cell wall extract derived from a non-pathogenic strain of *Mycobacterium* species. A presently preferred Mycobacterium extract is EQUIMUNE, a deprotenized highly purified cell wall extract derived from non-pathogenic strains of *Mycobacterium* species (Vetrepharm Research Inc., Athens, Ga.). Yet another embodiment contemplates the use of aluminum hydroxide as the adjuvant. Given the teachings and protocols provided herein for testing adjuvants, other adjuvants known in the art can be tested and utilized.

The vaccine protocol used in administer the immunogenic amount can vary depending upon the species, size and condition of the bird. The vaccine of the invention is typically administered parenterally, either subcutaneously or intramuscularly by injection. Of course, the immunogenic amount can be given in divided doses or administered at multiple sites in the bird. Booster immunizations can be given utilizing vaccines containing whole inactivated avian polyomavirus or any immunogenic portion thereof.

In one embodiment, the invention specifically provides a composition which produces an anamnestic response against avian polyomavirus infection in a sensitized bird which is classified as being a member of the *Psittaciformes* order, comprising an anamnestic response inducing amount of a recombinant protein of avian polyomavirus and a pharmaceutically acceptable carrier. As used herein, the term "anamnestic response" means a secondary (booster) immune response in a sensitized bird. By "sensitized bird" is means a bird which has been previously been in contact with avian polyomavirus antigen either by natural exposure to the virus or by vaccination (primary immunization) with avian polyomavirus or an antigenic portion thereof.

The invention also provides the discovery that the VP1 protein of avian polyomavirus can be utilized either as the primary immunogen or as a booster to the immune response to primary vaccination against avian polyomavirus in a safe and efficient manner and with minimal stress to the vaccinated bird. In one embodiment, the invention provides a vaccine which is protective against avian polyomavirus infection in a bird which is classified as being a member of the *Psittaciformes* order, comprising an immunogenic amount of a recombinant protein derived from an avian polyomavirus and a pharmaceutically acceptable carrier. In a more preferred embodiment, the invention provides the vaccine comprising an immunogenic amount of the recombinant protein derived from an avian polyomavirus, a pharmaceutically acceptable carrier and an adjuvant suitable for use in a bird which is classified as being a member of the *Psittaciformes* order. In another embodiment the immunogenic amount of the recombinant protein derived from an avian polyomavirus is between about 1.0 mg. and about 3 mg.

Still another embodiment of the present invention provides a composition which produces an anamnestic (secondary) response against avian polyomavirus infection in a sensitized bird which is classified as being a member of the *Psittaciformes* order, comprising an anamnestic response inducing amount of a recombinant avian polyovirus VP1 capsid protein and a pharmaceutically acceptable carrier.

Briefly, the recombinant VP1 protein in one embodiment was produced in *E. coli* by cloning the gene that codes for this protein into the pFLAG expression vector (International Biotechnologies, New Haven, Conn.). The expressed protein was partially purified by affinity chromatography using an anti-FLAG monoclonal antibody and the composition prepared by adding the protein to sterile saline (Garcia, A. P., et al., "Diagnosis of polyomavirus infection in seedcrackers using DNA in situ hybridization," *J. Assoc. Avian Vet.*, 1993; Gaskin, 1989, see also Yeung AKH, et al. Studies on the immunoproperties of recombinant VP1 from budgerigar fledgling disease virus by cloning and expressing VP1 in *E. coli* [Dissertation]. University of Georgia, 1993; and Rodgers, Rebecca E.d., et al., "Purification of Recombinant Budgerigar Fledgling Disease Virus VP1 Capsid Protein and Its ability for In Vitro Capsid Assembly," *J. Virology*, Vol. 68, No. 5, pp. 3386–3390 (May 1994)).

Given the teachings provided herein one of skill in the art will realize that other recombinant proteins and polypeptide fragments from polyoma virus can be utilized as an immunogen. Such proteins, or fragments thereof, can, for example, be obtained by cloning nucleic acids encoding the polypeptide in an expression system capable of producing the antigenic polypeptide or fragments thereof.

Given the amino acid sequence of the avian polyomavirus antigens (see, e.g., O. Rott et al., *Virology*, 1988, 165: 74–86; GenBank Accession No. M20775; R. Stoll et al., *J. Gen Virology*, 1993, 74:229–237), one can synthesize, using standard peptide synthesis techniques, peptide fragments chosen to be homologous to immunoreactive regions of the antigen and to modify these fragments by inclusion, deletion or modification of particular amino acid residues in the derived sequences. Thus, synthesis or purification of an extremely large number of peptides derived from the antigen is possible. Such peptides can be used to immunize a member of the *Psittaciformes* order.

The amino acid sequences of the present polypeptides can contain an immunoreactive portion of avian polyomavirus antigen attached to sequences designed to provide for some additional property, such as solubility. The amino acid sequences of an avian polyomavirus antigen can include sequences in which one or more amino acids have been substituted with another amino acid to provide for some additional property, such as to remove/add amino acids capable of disulfide bonding, to increase its bio-longevity, alter enzymatic activity, or alter interactions, e.g., at the injection site or with gastric acidity if an oral administration of the vaccine is used. In any case, the peptide must possess immunogenicity.

Recombinant viral proteins or protein fragments can be tested to determine their immunogenicity by the methods taught in the examples or by other methods known in the art. Briefly, various concentrations of a putative immunogenically specific fragment are prepared and administered to a bird and the immunological response (e.g., the production of antibodies or cell mediated immunity) of the bird to each concentration is determined. The amount of antigen administered will depend upon the species, size and condition of the bird. Thereafter an animal so inoculated with the antigen can be exposed to virulent avian polyomavirus to test the potential vaccine effect of the specific immunogenic fragment. The specificity of the putative immunogenic fragment can be ascertained by testing sera, and other fluids or lymphocytes form the inoculated bird, for cross-reactivity with other closely related avian polyomaviruses. Once the immunogenicity of a viral fragment is established, the immunogenic amount to be administered to a particular bird can be determined by optimization procedures as taught herein and known in the art.

In addition to the *E. coli* expression vectors herein, there are numerous *E. coli* expression vectors known to one of ordinary skill in the art useful for the expression of antigenic avian polyomavirus proteins and polypeptide fragments. Other microbial hosts suitable for use include bacilli, such as *Bacillus subtilis*, and other enterobacteriaceae, such as Salmonella, Serratia, and various Pseudomonas species. In these prokaryotic hosts one can also make expression vectors, which will typically contain expression control sequences compatible with the host cell (e.g., an origin of replication). In addition, any number of a variety of well-known promoters will be present, such as the lactose promoter system, a tryptophan (Trp) promoter system, a beta-lactamase promoter system, or a promoter system for phage lambda. The promoters will typically control expression, optionally with an operator sequence, and have ribosome binding site sequences for example, for initiating and completing transcription and translation. If necessary an amino terminal methionine can be provided by insertion of a Met codon 5' and fused in-frame with the antigen. Also, the carboxy-terminal extension of the antigen can be removed using standard oligonucleotide mutagenesis procedures.

Additionally, yeast expression can be use. There are several advantages to yeast expression systems. First, evidence exists that proteins produced in a yeast secretion system exhibits correct disulfide pairing. Second, post-translational glycosylation is efficiently carried out by yeast secretory systems. The *Saccharomyces cerevisiae* pre-pro-alpha-factor leader regions (encoded by the *MF-alpha*-1 gene) is routinely used to direct protein secretion from yeast. The leader regions of pre-pro-alpha-factor contains a signal peptide and a pro-segment which includes a recognition sequence for a yeast protease encoded by the *KEX*2 gene: this enzyme cleaves the precursor protein on the carboxyl side of a Lys-Arg dipeptide cleavage-signal sequence. The antigen coding sequence can be fused in-frame to the pre-pro-alpha-factor leader regions. This construct is then put under the control of a strong transcription promoter, such as the alcohol dehydrogenase I promoter or a glycolytic promoter. The antigen coding sequence is followed by a translation termination codon which is followed by transcription termination signals. Alternatively, the antigen coding sequences can be fused to a second protein coding sequence, such as Sj26 or beta-galactosidase, used to facilitate purification of the fusion protein by affinity chromatography. The insertion of protease cleavage sites to separate the components of the fusion protein is applicable to constructs used for expression in yeast.

The DNA sequences can be expressed in hosts after the sequences have been operably linked to, i.e., positioned to ensure the functioning of an expression control sequence in an appropriate expression vector. These expression vectors are typically replicable in the host organisms either as episomes or as an integral part of the host chromosomal DNA. Commonly, expression vectors can contain selection makers, e.g., tetracycline resistance or hygromycin resistance, to permit detection and/or selection of those cells transformed with the desired DNA sequences (see, e.g., U.S. Pat. No. 4,704,362).

Polynucleotides encoding a variant polypeptide may include sequences that facilitate transcription (expression sequences) and translation of the coding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and, optionally, an enhancer for use in eukaryotic expression hosts, and, optionally, sequences necessary for replication of a vector.

One example of a eukaryotic expression vector is the baculovirus insect vector. Expression can be achieved for example in Spodoptera frugiperda (SF9) cells using the polyhedron promoter with the target nucleic acid upstream of the promoter.

It is specifically contemplated that the avian polyomavirus expressed proteins can be used as the anitgen for ELISA testing to identify the presence of avian polyomavirus antibodies from the blood or other specimens from birds.

The vaccines and compositions of the invention can include, as noted above, an effective amount of inactivated avian polyomavirus in combination with a pharmaceutically acceptable carrier and, in addition, may include other medicinal agents, pharmaceutical agents, carriers, adjuvants, diluents, etc. By "pharmaceutically acceptable" is meant a material that is not biologically or otherwise undesirable, i.e., the material may be administered to an individual along with the selected compound without causing any undesirable biological effects or interacting in a deleterious manner with any of the other components of the pharmaceutical composition in which it is contained. Actual methods of preparing dosage forms are known, or will be apparent, to those skilled in this art; for example, see Martin, E. W., Ed., *Remington's Pharmaceutical Sciences*, latest edition, Mack Publishing Co., Easton, Pa.

Parenteral administration is generally characterized by injection. Injectables can be prepared in conventional forms, either as liquid solutions or suspensions, solid forms suitable for solution or suspension in liquid prior to injection, or as emulsions. A more recently revised approach for parenteral administration involves use of a slow release or sustained release system, such that a constant level of dosage is maintained. See, e.g., U.S. Pat. No. 3,710,795.

The present invention also provides a method of preventing avian polyomavirus infection in a bird which is classified as being a member of the *Psittaciformes* order, comprising administering to the bird a vaccine comprising an immunogenic amount of an inactivated avian polyomavirus and a pharmaceutically acceptable carrier. The subject bird of the methods of the invention can be any of the various species of birds which are classified as being members of the *Psittaciformes* order including, but not limited to, the examples cited herein. Specifically provided, however, is a method of preventing avian polyomavirus infection in a bird which is classified as being a member of the *Psittaciformes* order, comprising administering to the bird a vaccine comprising an immunogenic amount of an inactivated avian polyomavirus and a pharmaceutically acceptable carrier, wherein the bird is selected from the group consisting of a macaw, an Amazon parrot, a conure, a cockatoo, a Pionus Parrot, and an African Grey Parrot.

Also provided is a method of preventing avian polyomavirus infection in a bird from a species which is classified as being a member of the *Psittaciformes* order, comprising administering to the bird a vaccine comprising an immunogenic amount of an inactivated avian polyomavirus which infects a bird from a different species of the *Psittaciformes* order and a pharmaceutically acceptable carrier.

In one embodiment, the vaccine utilized in the methods of the invention is derived from an isolated avian polyomavirus designated the L4 strain. Given the surprisingly broad species coverage of the L4 strain vaccine as provided herein, other strains of avian polyomavirus isolated from *Psittaciformes* bird can be utilized to produce the vaccines of the invention and utilized in the above methods to cross-protect multiple species of *Psittaciformes* with a single vaccine. The L6 strain is a strain which can also be utilized.

Any of the vaccines and compositions described herein can be utilized in the methods of the invention, where appropriate, to prevent infection with or booster immunity to avian polyomavirus in a subject bird. For example, the vaccine utilized in the methods of the invention can further comprise an adjuvant suitable for use in a bird which is classified as a member of the *Psittaciformes* order. The adjuvant can be a long chain polydispersed β (1, 4) linked mannan polymer interspersed with O-acetylated groups such as, e.g., ACEMANNAN or a deproteinzied highly purified cell wall extract derived form a non-pathogenic strain of Mycobacterium species such as, e.g., EQUIMUNE.

In the methods described herein, the administering step is typically performed by parenteral administration, i.e., subcutaneous or intramuscular injection of the vaccine into the subject bird. The immunogenic amount of vaccine utilized in the methods of the invention is the same as the provided for in the vaccines of the invention. Specifically, the immunogenic amount of the inactivated avian polyomavirus corresponds to a titer of between $10^{4.5} \text{TCID}_{50}$ and $10^{7} \text{TCID}_{50}$ for the avian polyomavirus before inactivation but especially about $10^{5.8} \text{TCID}_{50}$.

The methods of the invention can further comprise the step of administering at least one booster vaccine to the bird. One or more booster inoculations are typically administered at bi-weekly intervals. The booster vaccine can be any of the vaccine preparations contemplated herein. However, a preferred embodiment of the invention provides a method of preventing avian polyomavirus infection in a bird which is classified as being a member of the *Psittaciformes* order, the composition comprising administering to the bird a vaccine comprising an immunogenic amount of an inactivated avian polyomavirus and a pharmaceutically acceptable carrier. After the initial inoculation, at least one booster vaccine is administered to the bird. The booster vaccine is a composition which produces an anamnestic response against avian polyomavirus infection in a sensitized bird which is classified as being a member of the Psittaciformes order. The booster comprises an anamnestic response inducing amount of a recombinant protein of avian polyomavirus and a pharmaceutically acceptable carrier. The booster vaccine can be comprised of any recombinant protein derived from avian polyomavirus or an immunogenic polypeptide fragment thereof. In one embodiment, the recombinant protein is the VP1 capsid protein. Briefly, the first booster vaccine can be administered to the subject bird about two weeks following primary inoculation. If desired, a second booster can be administered in about two weeks.

A recombinant protein such as the VP1 protein produces a specific antibody response in the animal to only a portion of the virus. Such a response to a specific immunogenic protein greatly reduces the risks associated with either a primary immunization or with a booster vaccination. Reaction to the recombinant vaccine is therefore milder yet sufficiently immunogenic to generate in the bird a protective immunity to the virus. In addition to being safer and less stressful, vaccines derived from recombinant proteins are more economical to manufacture.

Throughout this application, various publications are referenced. The disclosures of these publications in their entireties are hereby incorporated by reference into this application in order to more fully describe the state of the art to which this invention pertains.

EXAMPLE 1

Inactivated Avian Polyomavirus Vaccine

Material and Methods

Virus: A stock strain of avian polyomavirus (passage level 6), recovered originally from infected budgerigars (*Melopsittacus undulatus*), was grown in chicken embryo fibroblasts in M199 (tissue culture medium supplemented) with 5% calf serum and was used for all the experiments described in this study. Flasks of infected cells were grown for 7 days and were then frozen and thawed three times. The suspended cells were homogenized using a glass bead homogenizer with 0.1 mm beads according to the manufacturer's recommendations. Beads and cellular debris were separated from the supernatant by centrifugation (300×g for 5 minutes). The virus-containing supernatant (50 ml) was serially diluted in a microtiter plate containing a 24-hour monolayer of primary chicken embryo fibroblasts. This preparation had an infectivity titer of $10^{4.3}TCID_{50}$ per ml.

The virus preparation was purified by isopycnic centrifugation. Initially, the cellular suspension was clarified by centrifugation. (7000×g for 45 minutes). The clarified supernatant was layered over 45% (w/v) sucrose in phosphate-buffered saline solution (PBSS, pH 7.2) and centrifuged (140,000×g, 2 hours, 4° C.) to obtain crude viral pellets. The virus was resuspended in PBSS, adjusted to 1.34 g/cc with cesium chloride, and centrifuged to equilibrium (270,000×g, 16 hours, 20° C.). The gradient was collected with a density gradient fractionator. Fractions containing purified virus were dialyzed against PBSS and stored at −20° C. Fifty microliters of the virus suspension was serially diluted in a microtiter plate containing a 24-hour monolayer of primary chicken embryo fibroblasts. Fractions containing purified virus were dialyzed against PBSS and stored at −20° C. The cesium chloride purified virus preparation had an infectivity titer of $10^{5.8}TCID_{50}$ per ml.

Virus neutralizing antibody assay: Polyomavirus neutralizing antibody titers were determined according to published procedures (30) with the exception that the chicken embryo fibroblasts were fixed with 95% ethanol and stained with crystal violet to detect CPE (cytopathic effect). Antibody titers were expressed as the reciprocal of the serum dilution that protected the chicken embryo fibroblasts from detectable cytopathic effects.

Vaccine preparation: The purified virus used to produce the vaccine had a titer of $10^{5.8}TCID_{50}$ per ml before inactivation. The purified virus was inactivated by adding a sufficient quantity of β-propiolactone to create a solution with a final concentration of 0.1% β-propiolactone. The solution was incubated with constant mixing at 37° C. for 4 hours. The mixture was then placed in a refrigerator at 4° C. overnight. This preparation was evaluated to demonstrate the virus had been inactivated by placing 50 μl of the β-propiolactone treated virus in a 24-hour monolayer of chicken embryo fibroblasts. A control vaccine was produced by making a PBSS solution that contained a final concentration of 0.1% β-propiolactone.

Vaccination protocol: Six 30-to 45-day-old Blue and Gold Macaw (*Ara ararauna*) chicks from an aviary with no previous history of clinical avian polyomavirus infections were used in this study. The chicks were divided randomly into 3 pairs and housed in groups of 2. The vaccinated and unvaccinated chicks were maintained in separate locations to reduce the possibility of inadvertent viral exposure in the unvaccinated chicks. Blood was collected by jugular venipuncture from all chicks on days 0, 10, 20, 30 and 37. On days 10, 20 and 30, two groups of chicks were vaccinated subcutaneously with 50 μl of inactivated polyomavirus suspension emulsified in 150 μl of an oil adjuvant. The third group of chicks was vaccinated on the same days subcutaneously with β-propiolactone mixed in 50 μl of PBSS emulsified in 150 μl of an oil adjuvant. The chicks were examined immediately after inoculation and four times each day to determine whether vaccination caused any immediate or delayed local or systemic reactions.

Challenge: All chicks were challenged with live virus on days 37, 39 and 52. The in vitro infectivity of the challenge inoculum was confirmed by demonstrating characteristic cytopathic effects when a 50-μl sample of the challenge inoculum was placed on a 24-hour monolayer of chicken embryo fibroblasts grown in microtiter plates as described above. On days 37 and 39, the chicks were administered 50 μl of virus suspension containing $10^{3.3}TCID_{50}$ of live virus. On day 52, the chicks were given $10^{4.5}TCID_{50}$ of live virus. On each day of challenge, two of the vaccinated chicks received 50 μl of virus preparation by the oral and intracloacal routes; another two 50 μl of virus preparation by intramuscular inoculation. One of the unvaccinated control birds received 50 μl of virus preparation by the oral and intracloacal routes; the other 50 μl of virus preparation by intramuscular inoculation. Blood was collected from the chicks by jugular venipuncture on days 37, 46, 59 and 68. The blood samples were allowed to clot, and the serum was collected and used to determine virus-neutralizing antibody titers as described above. The chicks were examined four times a day for clinical changes suggestive of an active infection or adverse response to challenge.

DNA probe detection of polyomavirus nucleic acid: Whole blood samples collected in sodium heparin (20 μl heparin per ml of blood) were obtained on days 37, 46, 59 and 68. Samples were processed for detection of polyomavirus nucleic acid using amplification procedures and viral-specific DNA probes according to a modification of published procedures (10). Cloacal swabs were collected from the chicks on days 10, 20, 37 and daily thereafter. The swabs were collected before feeding each morning. These swabs were processed for detection of polyomavirus nucleic acid, as described previously (10).

Results

None of the chicks used in this study had detectable levels of polyomavirus neutralizing (VN) antibodies at the beginning of the study. The virus used for vaccination did not induce detectable cytopathic effects in a monolayer of chicken embryo fibroblasts after 7 days of incubation confirming that it had been inactivated following the addition of β-propiolactone. The vaccinated chicks developed a transitory polyuria (24 hrs) the day after the first vaccination and were considered to be slightly lethargic for a 24-to-48 hour period starting two days after each vaccination. The VN antibody titers that developed in the chicks vaccinated with β-propiolactone-treated PBSS (controls) or with inactivated avian polyomavirus are listed in Table 1. The chicks inoculated with β-propiolactone-treated PBSS emulsified in an oil adjuvant remained seronegative throughout the prechallenge period. The first increase in VN titers in the chicks vaccinated with inactivated antigen was detected 20 days after the initial vaccination. By the 37th day after the initial vaccination, the VN titers ranged from 20 to 40, with a geometric mean titer of 28.

All of the chicks remained clinically normal following challenge with live virus. The unvaccinated chicks had a 6-to-7 fold increase in VN antibody titer, suggesting that an active infection had occurred. None of the vaccinated chicks had a significant increase (greater than 4 fold) in VN antibody titer following challenge (Table 2). All of the chicks vaccinated with oil-adjuvanted vaccine developed lesions at each site of subcutaneous inoculation. Two of the birds develop moderate reactions (subcutaneous mass <0.5 cm in diameter) and two developed severe reactions (subcutaneous mass >0.5 cm in diameter with skin necrosis).

Using DNA probes, viral nucleic acid could not be demonstrated in cloacal swabs collected from any of the chicks prior to challenge (day 37). Viral nucleic acid was detected in cloacal swabs from the unvaccinated chick exposed to live virus by oral and intracloacal routes on days 1 and 2 after challenge. Viral nucleic acid was detected in cloacal swabs from the unvaccinated chick exposed to live virus by the intramuscular route on days 2 and 3 after challenge. Using the same detection technique, viral nucleic acid could not be demonstrated in cloacal swabs from the vaccinated chicks at any time during the study. The DNA probes failed to demonstrate the presence of viral nucleic acid in the amplified products from any of the whole blood samples tested.

Discussion

The vaccine used in this study elicited polyomavirus neutralizing antibodies in all the vaccinates. The induced immunologic response protected the vaccinates from subsequent challenge with live virus. Although the sample size was small, all of the vaccinated chicks were resistant to infection, whereas the unvaccinated chicks became infected, suggesting that the inactivated vaccine used in this study was effective.

Viral replication did not appear to occur in the vaccinated chicks because there was no significant change (greater than 4 fold increase) in the VN antibody titers in these birds following challenge. An increase in titers would have indicated an active infection with an associated anamnestic response. Although the detectable immunologic response in the form of VN antibodies was low (geometric mean titer, 28), the vaccinated chicks were resistant to challenge suggesting that a protective immunogenic response occurred following vaccination. We did not determine whether the induced protection was the result of humeral or cellular responses, and the VN titers were used only as an indication that an immunogenic response had occurred following vaccination and challenge.

The demonstration of a 6-to-7 fold increase in polyomavirus VN antibodies in the unvaccinated chicks suggests that an active infection occurred in these chicks following exposure to live virus. However, the birds exhibited no clinical changes and the infection was considered to be subclinical. It has been previously reported that VN antibody titers of 1:10 are suggestive of (and titers>1:10 are positive for) previous exposure to avian polyomavirus. Following epornitics in aviaries containing mixed species of psittacine birds, VN antibody titers have been shown to range from 1:10 to 1:320. The chicks vaccinated in this study developed VN antibody titers that are considered positive following natural outbreaks. Following challenge, the unvaccinated chicks developed VN antibody titers that are in the high range of those reported in birds naturally exposed to the virus.

The fact that unvaccinated, challenged chicks did not develop the typical clinical changes associated with an avian polyomavirus infection is noteworthy. The demonstration of VN antibody titers in normal appearing birds following natural infections suggests that many birds exposed to polyomavirus develop subclinical infections. In some cases, these neutralizing antibodies have been found to persist, which has been interpreted as an indication of an ongoing infection (carrier bird). In other surveys, VN antibody titers were found to decrease suggesting that the birds were not being continuously stimulated antigenically by the virus. In this study, infections in the unvaccinated chicks may have remained subclinical because of the age of the birds at the time of virus exposure, attenuation in cell culture of the virus used for challenge, or decreased virulence in macaws of virus derived from budgerigars.

If the challenged chicks developed a subclinical infection because of attenuation of the virus in cell culture or because of host differences in susceptibility to budgerigar fledgling disease virus, it could be argued that a modified-live avian polyomavirus vaccine derived from budgerigars could be used to vaccinate larger psittacine birds. Given that an inactivated vaccine was shown in this study to prevent infection, it would appear unnecessary, and an excessive risk, to use an attenuated live virus vaccine to protect larger psittacine birds from avian polyomavirus infections. A modified-live virus vaccine for avian polyomavirus should not be considered for 3 reasons: 1) the seriousness of disease induced by avian polyomavirus, 2) the hypothesis that birds which recover from disease develop subclinical infections with subsequent shedding of the virus, and 3) the potential for an attenuated vaccine strain to revert to a virulent form.

The pathogenesis of polyomavirus infections in larger psittacine birds has not been investigated. The incubation period of the virus in larger psittacine birds has been estimated based on clinical observation to be less than 14 days, but this has not been confirmed experimentally. In this study, VN antibodies were first demonstrated 21 days after initial exposure of the unvaccinated chick to live virus by the oral and intracloacal routes. Because ingestion is probably one of the routes by which a natural infection occurs, this finding suggests that the virus is capable of infecting the host and inducing a detectable antibody response in less than 21 days following ingestion of the virus. An antibody response was first detected in the unvaccinated chick exposed by the intramuscular route 7 days after exposure. The rapid antibody response in the chick administered virus by IM injection would suggest that the virus is capable of infecting a host and inducing a detectable antibody response in less than 7 days following exposure to an infectious dose of virus by this route.

Virus was detected in the stool of the infected (unvaccinated) chicks several times during the first week after viral challenge. Because one of the infected chicks had been inoculated by the intramuscular route, the demonstration of viral nucleic acid on a cloacal swab indicates that virus was being excreted from the body by either the gastrointestinal or urinary tracts. The demonstration of viral nucleic acid in the cloacal swabs from the chick challenged by the oral and intracloacal routes was of unknown importance because it was not possible to distinguish between virus that had originated from the inoculum and virus that may have been present as a result of an active infection. The detection of viral nucleic acid from the cloaca of the unvaccinated chick challenged by the intramuscular route as early as 2 days after the initial injection indicates that the virus was transported quickly through the body following inoculation.

In addition to the presence of polyomavirus antigen in infected tissues, viral particles have been demonstrated by electron microscopy in the serum of some infected budgerigars, viral nucleic acid has been demonstrated in the blood of budgerigars, and viral nucleic acid has been demonstrated by the use of DNA probes in the serum of some larger psittacine species. In our study, viral nucleic acid was not detected by DNA probe analysis of blood collected from the vaccinated or unvaccinated chicks. This may reflect a transient period of viremia that occurred during an interval when blood samples had not been collected, the absence of viremia, or a lack of sufficient quantity of circulating virus to be detected by the DNA amplification and subsequent detection procedures.

The oil adjuvant used in this study caused reactions in the form of granuloma formation at the site of injection in all of the vaccinates. Two of the chicks had severe reactions that resulted in open, draining lesions. The frequency of adverse reactions associated with the oil-adjuvanted vaccine was considered unacceptable.

Sound hygienic practices, maintaining closed aviaries, preventing visitors from entering avian nurseries, and attempting to identify and isolate subclinical shedders using viral specific DNA probes are the only methods currently available for controlling this virus in companion and aviary birds. As is the case with many other viral-induced diseases in companion animals, the best method for preventing avian polyomavirus infections is likely to be through the widespread use of an effective vaccine.

EXAMPLE 2

A Suitable Adjuvant for *Psittaciformes*

A group of adult psittacine birds with representatives from 8 different genera was used to determine whether any of four commercially available adjuvants mixed with inactivated avian polyomavirus would induce the formation of anti-polyomavirus neutralizing antibodies without causing unacceptable adverse systemic or local reactions.

Materials and Methods

Birds: The study population included 26 adult psittacine birds: 2 Umbrella Cockatoos (*Cacatua alba*), 4 African Grey Parrots (*Psittacus erithacus erithacus*), 4 Ducorp's Cockatoos (*Cacatua ducorps*), 1 Sulphur-crested Cockatoo (*Cacatua sulphurea*), 1 Goffin's Cockatoo (*Cacatua goffini*), 1 Red-fronted Conure (*Aratinga wagleri wagleri*), 1 Pionus Parrot (*Pionus maximillani*), 1 Sun Conure (*Aratinga solstitialis*), 1 Yellow-Naped Amazon Parrot (*Amazona ochrocephala auropalliata*), 5 White-bellied Caiques (*Pionites leucogaster leucogaster*), 1 Golden Conure (*Aratinga guarouba*), 1 Green Conure (*Aratinga holochlora rubritorquis*), 1 Blue-crowned Conure (*Aratinga acuticaudata acuticaudata*), 1 Ringed-neck Parakeet (*Psittacula krameri krameri*) and 1 Blue and Gold Macaw (*Ara ararauna*). Nine of the birds were known to be carriers of avian polyomavirus because of intermittent detection of viral nucleic acid in their excrement using DNA probes and the detection of sustained high polyomavirus-neutralizing antibody titers for over one year.

Virus: A stock strain of budgerigar fledgling disease virus, isolated originally from infected budgerigars (*Melopsittacus undulatus*), was grown in chicken embryo fibroblasts in M199 with 5% calf serum. Infected cells were incubated 5 to 7 days. The culture flask were frozen and thawed three times, and the contents were pooled. Freeze-thawed suspensions were centrifuged (500×g for 10 minutes) at 4° C. to remove cellular debris and the supernatant was used as the stock virus. The infectivity titer of the stock virus was determined by making ten-fold serial dilutions in M199 with fetal calf serum. Fifth microliters of each dilution ($10^{-3}$ through $10^{-8}$) was inoculated in replicates of eight per dilution into flat bottom 96-well microtiter plates. To each well, 200 ul of packed chicken embryo fibroblasts (in M199 with 5% fetal calf serum) was then added in a ratio of 1:200, respectively. Plates were incubated for 6 days, fixed with 95% ethanol, stained with crystal violet, and evaluated for cytopathic effects (CPE). The Spearman-Karber method was used to calculate the $TCID_{50}$ of the stock virus preparation. The infectivity titer of the virus preparation used for vaccination on days 0 and 14 was approximately $10^7$ $TCID_{50}$ per ml and the infectivity titer of the virus preparation used for all other vaccinations was approximately $10^9$ $TCID_{50}$ per ml.

Vaccine preparation: The virus used for vaccination was produced as described above except that the growth media was changed to M199 without calf serum 24 hours after the cell cultures were inoculated. The virus was inactivated by adding β-propiolactone. After 1 ml of β-propiolactone (95% solution) was added to 500 ml of virus preparation, the pH was adjusted to 7.0 by the addition of 1N sodium hydroxide (NaOH). This mixture was stirred constantly at room temperature overnight. One microliter of β-propiolactone (95% solution) was then added to 1000 ml of virus preparation and the pH adjusted to 7.0 by the addition of 1N NaOH. This mixture was maintained at room temperature and stirred constantly for 2 hours. The β-propiolactone was then neutralized by the addition of 1 ml of 0.2M sodium thiosulfate per 100 ml of virus suspension. The mixture was stored at 4° C. until used. This preparation was assayed for infectivity to insure complete virus inactivation by placing 50 μl of the β-propiolactone treated virus preparation on chicken embryo fibroblasts as described above.

Two birds were vaccinated with 500 μl of β-propiolactone treated virus only (Table 3). Twenty-two birds were vaccinated with β-propiolactone treated virus mixed with one of four adjuvants. The adjuvants used included: Acemannan, a long chain polydispersed β (1,4) linked mannan polymer interspersed with O-acetylated groups; Equimune, a deproteinized highly purified cell wall extract derived from non-pathogenic strains of Mycobacterium sp., and E3, an immunomodulator derived from the cell wall of *E. coli*. The β-propiolactone treated virus was mixed with each of the adjuvants so that the final suspension for inoculation contained 500 μl of inactivated virus. For the oil-adjuvanted vaccine, each dose represented a volume of 300 μl of mineral oil that had been mixed with 500 μl of β-propiolactone treated virus. For the Acemannan and E3 vaccines, 100 μl of each adjuvant was mixed with 500 μl of β-propiolactone treated virus. For the Equimune vaccine, 50 μl of adjuvant was mixed with 500 μl of β-propiolactone treated virus.

Two birds were vaccinated with recombinant VP1 protein emulsified in mineral oil. Recombinant VP1 protein was produced in E. coli by cloning the gene that codes for this protein into the pFLAG expression vector. The expressed protein was partially purified by affinity chromatography using an anti-FLAG monoclonal antibody. Twenty-five milligrams of protein (as determined using the Bradford reagent) was added to 500 μl of sterile saline solution and mixed with 300 μl of mineral oil.

Vaccination protocol: All injections and blood collections were performed with the birds under isoflurane anesthesia. Blood was collected by jugular venipuncture from each vaccinate on days 0, 14, 28, 42, 49 and 63. After blood collection, contour feathers were removed from the caudal proventer region and the birds were inoculated subcutaneously on days 0, 14 and 28. Alternating sides of the proventer region were used for each inoculation to help distinguish which of the injections was associated with a reaction.

The birds were divided into two groups on day 42 to determine the gross or clinically detectable systemic affects of repeated exposure and intramuscular inoculation with the two most promising adjuvants. Half the birds were vaccinated with Acemannan-antigen and half were vaccinated with Equimune-antigen by deep intramuscular injection into the pectoral muscle on days 42 and 49. Preparation of the vaccine for intramuscular inoculation was the same as described above.

Grading reactions: The birds were examined immediately after inoculation and daily to determine whether the vaccine caused any immediate or delayed local or systemic reactions. The injection sites were observed and palpated at each booster time for the presence of hyperemia, discoloration of the skin, swelling, thickening of the skin, necrosis, and abscess or scab formation. The size and location of each reaction was recorded according to the scheme: 0=no reaction; 1=slight reaction (hyperemia, skin discoloration); 2=mild reaction (small scab formation, thickening of the skin); 3=moderate reaction (subcutaneous mass<0.5 cm in diameter or <0.5 cm area of necrosis); 4=severe reaction (>0.5 cm subcutaneous mass, or >0.5 cm area of necrosis).

Virus neutralizing antibody assay: To detect virus neutralizing antibodies, blood collected from each bird was placed in sodium EDTA, allowed to settle, and the plasma was separated by centrifugation. The plasma was stored at −20C until assayed. Polyomavirus neutralizing antibody titers were determined as previously described except that the chicken embryo fibroblasts were fixed with 95% ethanol and stained with crystal violet to detect CPE. Antibody titers were expressed as the reciprocal of the serum dilution that protected the chicken embryo fibroblasts from detectable cytopathic effects as detected by reduced staining with crystal violet. Rabbit anti-polyomavirus antibodies with a VN titer of 1:1024 and normal chicken serum with a VN titer of <1:2 were used as positive and negative controls, respectively.

Results

Cytopathic effects (CPE) were not observed in chicken embryo fibroblast inoculated with β-propiolactone treated virus indicated that the virus used for vaccination in this study had been inactivated. Eighty-six percent (18 of 21) of the birds vaccinated with inactivated avian polyomavirus seroconverted (greater than four fold increase in VN antibody titer with the resulting titer>1:10) by two weeks after the third vaccination (day 42, Table 3). Three birds (#1, #22 and #23) died following the second booster inoculation with the E3-adjuvanted vaccine and were unavailable for titer calculations after day 28. Two other birds (#20 and #25) that did not seroconvert following subcutaneous vaccination were from the E3 adjuvanted vaccine group and did not receive a third booster vaccination. However, these latter birds also failed to seroconvert when vaccinated by the intramuscular route with antigen mixed with either Acemannan or Equimune (Table 2). One-hundred percent (13 of 13) of the birds vaccinated with antigen alone or antigen mixed with mineral oil or Acemannan seroconverted by the second week after the third inoculation (day 42, Table 3).

For each vaccinate, the highest VN antibody titer detected by the second week after the third vaccination (day 42) in the oil-adjuvanted group ranged from 1:16 to 1:131,072 (geometric mean titer GMT=724), in the antigen only group ranged from 1:16 to 1:1024 (GMT=128), in the E3 group ranged from 1:4 to 1:16,384 (GMT=54), in the Acemannan group ranged from 1:16 to 1:8192 (GMT=256) and in the Equimune group ranged from 1:8 to 1:131,072 (GMT=2580). One of two birds that were seropositive at the start of the study (#10 and #14) did seroconvert following vaccination with recombinant VP1 mixed in an oil adjuvant. These birds were inoculated with this vaccine to determine whether the rVP1 protein was immunogenic.

Of the vaccinates that were seropositive (VN antibody titer>1:10) prior to vaccination, 100% (7 of 7, bird #1 died following the second vaccination and is not included) seroconverted by two weeks after the second vaccination (day 28, Table 6). Of the birds that were seronegative (VN antibody titer<1:10) prior to vaccination, 71% (10 of 14) of these initially seronegative birds seroconverted by two weeks after the second vaccination (day 28, Table 6).

The use of E3 as an adjuvant was discontinued when three vaccinates died within two days of each other after the second inoculation. In these birds, necropsy findings considered relative to the vaccination procedure, included focal severe necrotizing dermatitis and myositis at the site of vaccination (all three birds), myeloid hyperplasia in the bone marrow suggestive of a heterophilic response to tissue necrosis (1 bird), Shwartzman reaction in the kidney (1 bird), and diffuse Gram-negative septicemia (1 bird).

Birds at the beginning of the study that had positive antibody titers developed higher VN antibody titers by the second week after the third subcutaneous vaccination than those birds that were considered seronegative at the beginning of the study (Table 6). However, the relative increase in titers was virtually the same, with a 4.2-fold increase in antibody titer in the seronegative group and a 4.1-fold increase in antibody titer in the seropositive group. The highest titers measured by the second week after the third subcutaneous vaccination (day 42) in the seropositive group ranged from 1:512 to 1:131,072 (GMT=8192, bird #1 not included) while the highest titers in the seronegative group ranged from 1:4 to 1:1024 (GMT=35, birds #22 and #23 not included).

All vaccination-induced lesions were allowed to resolve without treatment to observe the natural progression of the lesions (Table 5). None of the birds developed lesions that were considered to be inducing undue distress or pain. The appetites and attitudes of the birds remained normal throughout the study except for one caique (#14) that exhibited a 3-day period of depression and lethargy after the second vaccination. This bird recovered uneventfully.

All of the birds (6 of 6) vaccinated with oil-adjuvanted vaccine developed some type of lesion after subcutaneous inoculation. These reactions were classified as moderate to severe. Half of the birds in this group that developed lesions were seronegative at the start of the study and half of the birds were seropositive. One of the birds (#21) in the non-adjuvanted vaccine group developed a mild reaction characterized by hyperemia and thickening of the skin. Reactions in the surviving members of the E3 group were considered mild. The cutaneous and subcutaneous lesions in the birds that died were considered clinically mild, but histologically severe. The reactions in the Equimune group were considered mild. Acemannan was considered the least reactive adjuvant, with one vaccinate developing a slight reaction (hyperemia) following the initial vaccination. None of the birds vaccinated by the intramuscular route with Acemannan or Equimune developed visible or palpable reactions. No difference was noted with respect to reactions in the birds that were either seropositive or seronegative at the start of the study.

Discussion

In general, the advantage of oil-adjuvanted vaccines in comparison to other immunization products is their ability to induce durable immunity when mixed with an inactivated antigen. However, a history of adverse reactions in some Psittaciformes vaccinated with oil-adjuvanted vaccines created the need for an alternative adjuvant for use with inactivated antigens intended for administration in this order of birds. Another disadvantage of oil-adjuvanted vaccines is that their high viscosity makes them difficult to deliver. An alternative adjuvant that stimulates immunity, mixes with antigen easily, and is simply administered would be preferable.

The products used in this study as adjuvants were chosen because of their immunomodulating characteristics. Acemannan has been shown to have antiviral, adjuvant, and immunomodulatory functions. This compound has been licensed for use with a Marek's disease virus and turkey herpesvirus vaccine. Equimune has been used as an enhancer of the immune response in conjunction with viral vaccines for upper respiratory diseases in horses. E3 has been used as an immunomodulator in the production of vaccines for companion animals.

Example 1 had shown that an oil-adjuvanted inactivated avian polyomavirus vaccine induced an immunologic response that protected Blue and Gold Macaw chicks from subsequent challenge with cell culture-derived avian polyomavirus. In these birds, a VN titer as low as 1:20 correlated with a protective response; whether the humor or cellular response provided the demonstrated protection is unknown. A VN antibody titer of >1:10 traditionally has been considered positive for avian polyomavirus antibodies.

Some of the birds used in this study were considered to be polyomavirus carriers for two reasons; the demonstration of viral nucleic acid in cloacal swabs using DNA amplification procedures and demonstration of sustained high antibody titers (over one year of sustained high titers). Birds that were seropositive were used in this study to determine whether an adjuvated inactivated avian polyomavirus vaccine would cause any adverse reactions in birds that already had a VN titer to polyomavirus from a previous or sustained infection. The initially seropositive birds used in this study developed no observable adverse reactions following vaccination that were not attributable to the adjuvant.

The birds in this study were initially vaccinated by the subcutaneous route, and several adjuvants were used. After the initial series of subcutaneous vaccinations, the birds were vaccinated by the intramuscular route using either Acemannan or Equimune as adjuvants. Repeated exposure to these vaccines was intended to determine whether unacceptable local or clinically detectable systemic reactions might occur following frequent vaccination with the most promising adjuvants.

Reactions at the injection site varied with the type of adjuvant. The oil-adjuvanted reactions were moderate to severe, whereas the reactions with the other adjuvants were slight, mild, or undetectable. The oil-adjuvanted vaccine caused lesions that included severe granuloma formation and necrosis. In all, each bird was exposed to a minimum of 5 injections with an adjuvanted antigen (except for the E3 group that received 4 inoculations) over a 7-week period. The Acemannan and Equimune adjuvants did not cause unacceptable reactions even following this high frequency of exposure to the adjuvant antigen mixture. Considering the ease of administration and the mild post-vaccinational reactions, a vaccine that contains an alternative adjuvant to oil would appear to be the most efficacious for use with avian polyomavirus in psittacine birds.

The fact that 81% (17 of 21) of the vaccinates seroconverted by two weeks after the second vaccination suggests that no more than two vaccinations may be necessary to induce a sufficient immunologic response in the susceptible population to control this disease.

EXAMPLE 3

Primary Immunization of *Psittaciformes* with VP1 Protein

We have evaluated the immunogenicity of a recombinant VP1 this protein in a chicken model utilizing 2 chickens with 1 chicken serving as a control. Serum was collected from the birds on days 0, 14, 28, and 42. The 2 vaccinates received 2 milligrams of a Bacculovirus derived VP-1 protein without adjuvant injected intramuscularly on days 0 and 14. The birds were seronegative prior to vaccination and a VN antibody titer of 20 was detected on day 28. When the serum was tested on day 42, the VN antibody titer had decayed to an undetectable level. The birds were then boosted twice at 2-week intervals with VP-1 protein mixed in aluminum hydroxide. Two weeks after the last boost, the VN titers and these birds were 80 and 320.

EXAMPLE 4

Delivery of Recombinant Avian Polyomavirus Protective Antigens Via Genetic Immunization Nucleic acid vaccine vectors suitable for genetic, or "naked nucleic acid", immunization are constructed using any of a variety of cis-acting transcription/translation regulatory sequences known in the art. General methods for the construction, production and administration of nucleic acid vaccines are known in the art, e.g. Vogel, F R and N Sarver (1995) *Clin. Microbiol. Rev.* 8:406–410.

These vaccines for avian polyomavirus comprise nucleic acids that functionally encode avian polyomavirus polypeptides or fragments thereof. For example, to functionally encode, i.e., allow the nucleic acid to be expressed, the nucleic acid can include, for example, expression control sequences, such as a cis-acting transcription/translation regulatory sequence (comprising one or more of the following: a promoter, response element(s), an initiator sequence), an enhancer, and information processing sites, such as ribosome binding sites, RNA splice sites, intron elements, polyadenylation sites, and transcriptional terminator sequences, all of which, either alone or in combinations, are capable of directing expression in the target animal. Preferred expression control sequences are strong and/or inducible cis-acting transcription/translation regulatory sequences such as those derived from metallothionine genes, actin genes, myosin genes, immunoglobulin genes, cytomegalovirus (CMV), SV40, Rous sarcoma virus, adenovirus, bovine papilloma virus, etc. The avian polyomavirus nucleic acid and expression control sequences are constructed in a vector, such as a plasmid of bacterial origin, for administration to the target animal. There are numerous plasmids known to those of ordinary skill in the art useful for the production of nucleic acid vaccine plasmids. A specific embodiment employs constructs using the plasmid "pcDNA3.1+" as the vector (InVitrogen Corporation, Carlsbad, Calif.). In addition, the avian polyomavirus vector construct may contain immunostimulatory sequences ("ISS") that stimulate the animals' immune system. Other possible additions to the nucleic acid vaccine constructs include nucleic acid sequences encoding cytokines, such as granulocyte macrophage colony stimulating factor (GM-CSF) or interleukin-12 (IL-12). The cytokines can be used in various combinations to fine-tune the response of the animal's immune system, including both antibody and cytotoxic T lymphocyte responses, to bring out the specific level of response needed to protect the animal from the targeted disease.

Alternatively, nucleic acid vaccines can be constructed in a non-replicating retroviral vector, such as the Moloney murine leukemia virus (N2) backbone described by Irwin, et al. (1994, J. Virology 68:5036–5044).

Modifications to the above-described nucleic acid vaccines are also contemplated, since, for example, mutations can thereby be studied for greater protective vaccine effect. Additionally, modifications that can be useful are modifications to the sequences controlling expression of the avian polyomavirus sequences, such as modifications to make production of the polypeptides inducible or repressible upon addition to the cells of the appropriate inducer or repressor. Other modifications can be made, as known to the artisan. Such modifications are standard in the art (see, e.g., Sambrook et al., *Molecular Cloning: A Laboratory Manual*, 2nd Ed., Cold Spring Harbor Laboratory, Cold Spring Harbor, N.Y., 1989). The nucleic acids can be generated by means standard in the art, such as by recombinant nucleic acid techniques, as exemplified in the examples herein, and by synthetic nucleic acid synthesis or in vitro enzymatic synthesis.

Nucleic acid vaccines are administered in an immunogenic amount by methods known in the art. Preferably, nucleic acid vaccines are administered intramuscularly by injection, but other methods of administration are contemplated. In one embodiment, the immunogenic amount of a nucleic acid vaccine for birds is between 5 and 100 micrograms.

One nucleic acid vaccine construct contains the pcDNA3.1+ vector with an avian polyomavirus DNA fragment which encodes the agnogene sequence, the VP2/VP3 overlapping open reading frames (orfs), and the VP1 orf. This fragment, based on the nucleotide numbering assignments in GenBank Accession No. M20775, comprises nucleotides 766–2943 (SEQ ID NO:1). An alternative construct does not contain the agnogene sequence, and thus comprises nucleotides 966–2938 (SEQ ID NO:2).

The nucleic acid vaccine construct described above was produced in *E. coli,* and the plasmid was purified using commercially available DNA purification columns. Chickens were injected with 50 μg plasmid intramuscularly. The birds received a booster vaccination of 50 μg two weeks after the initial injection. Blood was collected from the birds approximately three months following the initial vaccination, and antibodies against avian polyomavirus were present in the blood of vaccinated birds (see the results presented below). Birds are boosted annually or as deemed necessary.

Antibody Results

| Bird Treatment | Antibody Titer* Prior to Vaccination | Antibody Titer* 3 mos. after Vaccination |
| --- | --- | --- |
| Control | 0.018 | 0.179 |
| SEQ ID NO:2 Construct | | |
| Bird #154 | 0.022 | 0.315 |
| Bird #155 | 0.016 | 0.382 |
| SEQ ID NO:1 Construct | | |
| Bird #156 | 0.023 | 0.409 |
| Bird #157 | 0.026 | 0.559 |
| Inactivated Polyomavirus Vaccine | | |
| Bird #162 | 0.021 | 0.357 |
| Bird #163 | 0.012 | 0.483 |

*Presented as O.D. (at 405 nm) readings from ELISAs, using whole virus as antigen Other nucleic acid vaccines of the invention are constructed using nucleic acid sequences encoding one or more of the following open reading frames: VP1 (SEQ ID NO: 8), VP2 (SEQ ID NO: 4), and VP3 (SEQ ID NO: 6). These nucleic acid vaccines can be constructed with or without sequence encoding the agnogene orf (SEQ ID NO: 10). Specific embodiments are constructed using nucleic acid sequences for VP1, VP2 and VP3 as set forth as SEQ ID NOS: 7, 3, and 5, respectively, with or without the sequence for the agnogene orf as set forth in SEQ ID NO: 9.

Although the present process has been described with reference to specific details of certain embodiments thereof, it is not intended that such details should be regarded as limitations upon the scope of the invention except as and to the extent that they are included in the accompanying claims. The text of the references cited herein are hereby incorporated in their entirety by reference.

REFERENCES

1. Davis R B, Bozeman L H, Gandry O J, et al. A viral disease of fledgling budgerigars. Avian Dis 1981; 25:179–183.
2. Bozeman L H, Davis R B, Gandry D, et al. Characterization of a papovavirus isolated from fledgling budgerigars. Avian Dis 1981; 25:972–980.
3. Bernier G, Morin M, Marsolais G. A generalized inclusion body disease in the budgerigar (*Melopsittacus undulatus*) caused by a papovavirus-like agent. Avian Dis 1981; 25:1083–1092.
4. Dykstra M J, Dykstra C C, Lukert P D, et al. Investigations of budgerigar fledgling disease virus. Am J Vet Res 1984; 45:1883–1887.
5. Lehn H, Muller H. Cloning and characterization of budgerigar fledgling disease virus (BFDV), an avian polyomavirus. Virology 1986; 151:362–370.
6. Jacobson E R, Hines S A, Quesenberry K, et al. Epornitic of papova-like virus-associated disease in a psittacine nursery. J Am Vet Med Assoc 1984; 185:1337–1341.

7. Clubb S L, Davis R B. Outbreak of papova-like viral infection in a psittacine nursery—a retrospective view. Proc Assoc Avian Vet. Toronto: 1984: 121–129.
8. Graham D L. An update on selected pet bird virus infections. Proc Assoc Avian Vet. Toronto: 1984: 267–280.
9. Lowenstein L J. Emerging viral diseases of psittacine birds. In: Kirk R W, ed. Current Veterinary Therapy IX. Philadelphia: W B Saunders, 1986: 205–710.
10. Niagro F D, Ritchie B W, Latimer K S, et al. Use of polymerase chain reaction for detection of BFD in suspect birds. Proc Assoc Avian Vet. Phoenix: 1990: 25–37.
11. Phalen D N, Ambrus S, Graham D L. The avian urinary system: Form function diseases. Proc Assoc Avian Vet. Phoenix: 1990: 44–57.
12. Garcia A P, Latimer K S, Niagro F D, et al. Diagnosis of polyomavirus infection in seedcrackers using DNA in situ hybridization. J Assoc Avian Vet 1993.
13. Gaskin J M. Psittacine viral disease: A perspective. J Zoo Wildl Med 1989; 20:249–264.
14. Johnston K M, Riddell C. Intranuclear inclusion bodies in finches. Can Vet J 1986; 27:432–434.
15. Marshall R. Papova-like virus in a finch aviary. Proc Assoc Avian Vet. 1989: 203–207.
16. Schmidt R E, Goodman G J, Higgins R J, et al. Morphologic identification of papovavirus in a Moluccan cockatoo (*Cacatua molucensis*) with neurologic signs. Assoc Avian Vet Today 1987; 1:107–108.
17. Pass D A, Prus S E, Riddell C. A papova-like virus infection of splendid parakeets (*Neophema splendida*). Avian Dis 1987; 31:680–684.
18. Pass D A. A papova-like virus infection of lovebirds (Agapornis sp.). Aust Vet J 1985; 82:318–319.
19. Gough J F. Outbreaks of budgerigar fledgling disease in three aviaries in Ontario. Can Vet J 1989; 30:672–674.
20. Bernier G, Morin M, Marsolais G. Papovavirus-induced feather abnormalities and skin lesions in the budgerigar: Clinical and pathological findings. Can Vet J 1984; 25:307–310.
21. Hirai K, et al. Isolation of a papova-like agent from young budgerigars with feather abnormalities. J Vet Sci 1984; 46:577–587.
22. Pascucci S, Maestrini N, Misciattelli M, et al. Malattia da virus papova-simile nel papagallino ondulato (*Melopsittacus undulatus*). Clin Med (Milan) 1983; 106:38–41.
23. Sztojkov V, Saghy E, Meder M, et al. A hullamous papagaj (*Melopsittacus undulatus*) papovavirus okozta megbetegedesenek hazai megallapitasa. Magy Alla. Lapja 1985; 40:59–63.
24. Krautwald M-E, Kaleta E F. Relationship of French moult and early virus induced mortality in nestling budgerigars. Proc 8th Intl Cong World Vet Poult Assoc. 1985: 115.
25. Davis R B, Lukert P D, Avery P. An update on budgerigar fledgling disease (BFD). Proc 33rd West Poult Dis Conf. 1984: 96–97.
26. Gaskin J M. The serodiagnosis of psittacine viral infections. AAV, Honolulu: 1988: 7–10.
27. Lynch J, Swinton J, Pettit J, et al. Isolation and experimental chicken-embryo-inoculation studies with budgerigar papovavirus. Avian Dis 1984; 28:1135–1139.
28. Wainwright P O, Lukert P D, Davis R B, et al. Serological evaluation of some psittaciformes for budgerigar fledgling disease virus. Avian Dis 1987; 31:673–676.
29. Davis R B. Budgerigar fledgling disease (BFD). 32nd West Poult Dis Conf. 1983: 104.
30. Lukert P D. Budgerigar fledgling disease. In: Purchase H G, et al, ed. A Laboratory Manual for the Isolation and Identification of Avian Pathogens. Kennet Square: Am Assoc Avian Pathol, 1989: 106–107.
31. Graham D L, Calnek B W. Papovavirus infection in hand-fed parrots: Virus isolation and pathology. Avian Dis 1986; 31:398–410.
32. Phalen D N, Wilson V G, Graham D L. Polymerase chain reaction assay for avian polyomavirus. J Clin Microbiol 1991; 29:1030–1037.
33. Gaskin J M. Adverse reactions to current pet bird vaccines. J AAV 1991; 5:12–14.
34. Curtis-Velasco M. Vaccination reaction in umbrella cockatoos. J AAV 1990; 4:206.
35. Schmidt R E. From a pathologist's perspective. J Assoc Avian Vet 1991; 5:10.
36. Curtis-Velasco M. Vaccination reaction in umbrella cockatoos. J AAV 1990;4:206.
37. Curtis-Velasco M. Further vaccine reactions. J Assoc Avian Vet 1991;5:10.
38. Fudge A M. High risk birds still benefit. J Assoc Avian Vet 1991;5:10–11.
39. Leonard J M. Follow-up on vaccine reaction reports. J Assoc Avian Vet 1991;5:11–12.
40. Gaskin J M. Adverse reactions to current pet bird vaccines. J AAV 1991;5:12–14.
41. Harrison G J. The vaccine dilemma. J Assoc Avian Vet 1991; 5:7.
42. Droual R, et al. Investigations of problems associated with intramuscular breast injection of oil-adjuvanted killed vaccines in chickens. Avian Dis 1990;34:473–478.
43. Amyx H L. Control of animal pain and distress in antibody production and infectious disease studies. J Am Vet Med Assoc 1987;191:1287–1289.
44. Niagro F D, et al. Avian polyomavirus. Discordance between neutralizing antibody titers and viral shedding in an aviary. Proc Assoc Avian Vet. 1991: 22–26.
45. Gaskin J M. The serodiagnosis of psittacine viral infections. Assoc Avian Vet. Honolulu: 1988: 7–10.
46. Villegas P, Purchase G H. Titration of biological suspensions. In: Hitchner S B, et al., (eds). Isolation and Identification of Avian Pathogens. Endwell: Creative Publishing Co, 1980:
47. Lin K H, Cheng S Y. An efficient method to purify active eukaryotic proteins from the inclusion bodies in *E. coli*. Biotechnics 1991;11:748–753.
48. Yeung A K H, et al. Studies on the immunoproperties of recombinant VP1 from budgerigar fledgling disease virus by cloning and expressing VP1 in *E. coli* [Dissertation]. University of Georgia, 1993.
49. Bradford M M. A rapid and sensitive method for the quantitation of microgram quantities of protein utilizing the principle of protein-dye binding. Anal Biochem 1976;72:248–254.
50. Lukert P D. Budgerigar fledgling disease. In: Purchase H G, et al, ed. A Laboratory Manual for the Isolation and Identification of Avian Pathogens. Kennet Square: Am Assoc Avian Pathol, 1989: 106–107.
51. Schmidt R E. From a pathologist's perspective. J Assoc Avian Vet 1991;5:10.
52. Sheets M A, et al. Studies of the effect of Acemannan on retrovirus infections: Clinical stabilization of feline leukemia virus infected cats. Molec Biotheras 1991;(3): 41–45.
53. Tizard I R. Use of immunomodulators as an aid to clinical management of feline leukemia virus-infected cats. J Am Vet Med Assoc 1991;199:1482–1485.

54. Clubb S L, Davis R B. Outbreak of papova-like viral infection in a psittacine nursery—a retrospective view. Proc Assoc Avian Vet. 1984: 121–129.
55. Jacobson E R, et al. Epornitic of papova-like virus-associated disease in a psittacine nursery. J Am Vet Med Assoc 1984;185:1337–1341.
56. Wainwright P O, et al. Serological evaluation of some psittaciformes for budgerigar fledgling disease virus. Avian Dis 1987;31:673–676.
57. Rodgers, Rebecca E. D., et al., "Purification of Recombinant Budgerigar Fledgling Disease Virus VP1 Capsid Protein and Its ability for In Vitro Capsid Assembly," J. Virology, Vol. 68, No. 5, pp. 3386–3390
58. Rott, O, M Korger, H Muller, and G Hobom, 1988, The Genome of Budgerigar Fledgling Disease Virus, an Avian Polyomavirus; Virology 165: 74–86.

What is claimed is:

1. A nucleic acid vaccine vector comprising a eukaryotic cis-acting transcription/translation expression control sequence functionally linked to a nucleic acid encoding an immunogenic avian polyomavirus polypeptide, wherein the cis-acting transcription/translation expression control sequence comprises a promoter, whereby the nucleic acid vaccine vector when administered to a bird which is classified as a member of the *Psittaciformes* order, expresses the immunogenic avian polyomavirus polypeptide and is protective against avian polyomavirus infection in the bird, wherein the nucleic acid encoding an avian polyomavirus polypeptide comprises a sequence encoding the agnogene, VP2, VP3 and VP1.

2. The vaccine vector of claim 1, wherein the nucleic acid comprises the sequence set forth in SEQ ID NO:1.

3. A nucleic acid vaccine vector comprising a eukaryotic cis-acting transcription/translation expression control sequence functionally linked to a nucleic acid encoding an immunogenic avian polyomavirus polypeptide, wherein the cis-acting transcription/translation expression control sequence comprises a promoter, whereby the nucleic acid vaccine vector when administered to a bird which is classified as a member of the *Psittaciformes* order, expresses the immunogenic avian polyomavirus polypeptide and is protective against avian polyomavirus infection in the bird, wherein the nucleic acid encoding an avian polyomavirus polypeptide comprises a sequence encoding VP2, VP3 and VP1.

4. The vaccine vector of claim 3, wherein the nucleic acid comprises the sequence set forth in SEQ ID NO:2.

5. The vaccine vector of claim 1, further comprising an adjuvant suitable for use in a bird which is classified as being a member of the *Psittaciformes* order.

6. The vaccine vector of claim 3, further comprising an adjuvant suitable for use in a bird which is classified as being a member of the *Psittaciformes* order.

* * * * *